(12) United States Patent
Garibyan et al.

(10) Patent No.: US 11,826,427 B2
(45) Date of Patent: Nov. 28, 2023

(54) COMPOSITIONS AND METHODS FOR TREATMENT OF NEUROLOGICAL DISORDERS

(71) Applicant: The General Hospital Corporation, Boston, MA (US)

(72) Inventors: Lilit Garibyan, Newton, MA (US); Richard Rox Anderson, Boston, MA (US); William A. Farinelli, Boston, MA (US); Emilia Javorsky, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 69 days.

(21) Appl. No.: 17/236,567

(22) Filed: Apr. 21, 2021

(65) Prior Publication Data

US 2021/0236639 A1     Aug. 5, 2021

Related U.S. Application Data

(63) Continuation of application No. 15/505,039, filed as application No. PCT/US2015/047292 on Aug. 27, 2015, now abandoned.

(60) Provisional application No. 62/121,472, filed on Feb. 26, 2015, provisional application No. 62/121,329, filed on Feb. 26, 2015, provisional application No. 62/042,979, filed on Aug. 28, 2014.

(51) Int. Cl.
| | |
|---|---|
| A61K 45/06 | (2006.01) |
| A61K 9/00 | (2006.01) |
| A61K 47/02 | (2006.01) |
| A61K 47/10 | (2017.01) |
| A61K 47/26 | (2006.01) |
| A61K 33/00 | (2006.01) |
| A61K 31/045 | (2006.01) |
| A61K 31/047 | (2006.01) |
| A61K 31/137 | (2006.01) |
| A61K 31/7004 | (2006.01) |
| A61K 31/718 | (2006.01) |
| A61K 31/765 | (2006.01) |
| A61K 31/167 | (2006.01) |
| A61K 31/245 | (2006.01) |
| A61K 31/445 | (2006.01) |
| A61K 47/18 | (2017.01) |
| A61K 47/28 | (2006.01) |

(52) U.S. Cl.
CPC ............ *A61K 45/06* (2013.01); *A61K 9/0019* (2013.01); *A61K 9/0024* (2013.01); *A61K 31/045* (2013.01); *A61K 31/047* (2013.01); *A61K 31/137* (2013.01); *A61K 31/167* (2013.01); *A61K 31/245* (2013.01); *A61K 31/445* (2013.01); *A61K 31/7004* (2013.01); *A61K 31/718* (2013.01); *A61K 31/765* (2013.01); *A61K 33/00* (2013.01); *A61K 47/02* (2013.01); *A61K 47/10* (2013.01); *A61K 47/18* (2013.01); *A61K 47/26* (2013.01); *A61K 47/28* (2013.01)

(58) Field of Classification Search
CPC .............. A61K 2300/00; A61K 31/045; A61K 31/047; A61K 31/137; A61K 31/167; A61K 31/245; A61K 31/445; A61K 31/7004; A61K 31/718; A61K 31/765; A61K 33/00; A61K 45/06; A61K 47/02; A61K 47/10; A61K 47/18; A61K 47/26; A61K 47/28; A61K 9/0019; A61K 9/0024; A61P 13/02; A61P 17/00; A61P 17/02; A61P 17/04; A61P 17/06; A61P 17/08; A61P 19/02; A61P 23/02; A61P 25/00; A61P 25/02; A61P 25/04; A61P 25/08; A61P 35/00; A61P 37/08
See application file for complete search history.

(56) References Cited

U.S. PATENT DOCUMENTS

| | | |
|---|---|---|
| 4,883,665 A | 11/1989 | Miyazima et al. |
| 4,986,079 A | 1/1991 | Koseki et al. |
| 5,005,364 A | 4/1991 | Nelson |
| 5,143,063 A | 9/1992 | Fellner |
| 5,507,790 A | 4/1996 | Weiss |
| 5,769,879 A | 6/1998 | Richards et al. |
| 6,126,684 A | 10/2000 | Boyden et al. |
| 6,244,052 B1 | 6/2001 | Kasza |
| 6,413,444 B1 | 7/2002 | Kasza |
| 6,430,957 B1 | 8/2002 | Inada et al. |
| 6,962,601 B2 | 11/2005 | Becker et al. |
| 7,367,341 B2 | 5/2008 | Anderson et al. |
| 7,422,601 B2 | 9/2008 | Becker et al. |
| 7,507,234 B2 | 3/2009 | Utley et al. |

(Continued)

FOREIGN PATENT DOCUMENTS

| | | |
|---|---|---|
| CN | 105640642 A | 6/2016 |
| EP | 2561886 A1 | 2/2013 |

(Continued)

OTHER PUBLICATIONS

Lapid (Syringe-Delivered Tumescent Anesthesia Made Easier, Aesth Plast Surg (2011) 35:601-60).*
Hauser (Journal of Prolotherapy International Medical Editorial Board Consensus Statement on the Use of Prolotherapy for Musculoskeletal Pain, Journal of Prolotherapy | vol. 3 , Issue 4 | Dec. 2011).*
Sloviter (Effects of the Intravenous Administration of Glycerol Solutions to Animals and Man, Harrison Department of Surgical Research, School of Medicine, University of Pennsylvania, Philadelphia, Pa., 1958).*

(Continued)

*Primary Examiner* — Kathrien A Hartsfield
(74) *Attorney, Agent, or Firm* — Wolf, Greenfield & Sacks, P.C.

(57) ABSTRACT

Described herein are compositions comprising, and methods for using, biocompatible cold slurries and methods of administering the same to provide reversible inhibition of peripheral nerves in a subject in need thereof.

25 Claims, 13 Drawing Sheets

(56) References Cited

U.S. PATENT DOCUMENTS

| | | | |
|---|---|---|---|
| 7,897,141 | B2 | 3/2011 | Wheatley et al. |
| 8,505,315 | B2 | 8/2013 | Kasza et al. |
| 8,715,622 | B2 | 5/2014 | Wheatley et al. |
| 8,840,608 | B2 | 9/2014 | Anderson et al. |
| 9,980,076 | B1 | 5/2018 | Avram et al. |
| 10,582,960 | B2 | 3/2020 | Avram et al. |
| 2002/0107199 | A1 | 8/2002 | Walker |
| 2003/0032996 | A1 | 2/2003 | Hallman |
| 2003/0181897 | A1 | 9/2003 | Thomas et al. |
| 2004/0176755 | A1 | 9/2004 | Lafontaine |
| 2004/0210212 | A1 | 10/2004 | Maurice et al. |
| 2004/0215295 | A1 | 10/2004 | Littrup et al. |
| 2005/0203598 | A1 | 9/2005 | Becker et al. |
| 2005/0251120 | A1 | 11/2005 | Anderson et al. |
| 2006/0079869 | A1 | 4/2006 | Bischof et al. |
| 2006/0161232 | A1 | 7/2006 | Kasza et al. |
| 2006/0235375 | A1 | 10/2006 | Littrup et al. |
| 2007/0010861 | A1 | 1/2007 | Anderson et al. |
| 2007/0056313 | A1 | 3/2007 | Kasza et al. |
| 2007/0106247 | A1 | 5/2007 | Burnett et al. |
| 2008/0183164 | A1 | 7/2008 | Elkins et al. |
| 2008/0236186 | A1 | 10/2008 | Kasza et al. |
| 2008/0247957 | A1 | 10/2008 | Wheatley |
| 2008/0279783 | A1 | 11/2008 | Wheatley et al. |
| 2008/0300571 | A1 | 12/2008 | Lepivert |
| 2009/0028797 | A1 | 1/2009 | Wheatley et al. |
| 2009/0118722 | A1 | 5/2009 | Ebbers et al. |
| 2009/0234325 | A1 | 9/2009 | Rozenberg et al. |
| 2009/0255276 | A1 | 10/2009 | Kasza et al. |
| 2009/0301107 | A1 | 12/2009 | Kammer et al. |
| 2010/0036295 | A1 | 2/2010 | Altshuler et al. |
| 2010/0113615 | A1 | 5/2010 | Boyden et al. |
| 2010/0137304 | A1 | 6/2010 | Gilday et al. |
| 2010/0152880 | A1 | 6/2010 | Boyden et al. |
| 2010/0179527 | A1 | 7/2010 | Watson et al. |
| 2011/0009748 | A1 | 1/2011 | Greene et al. |
| 2012/0323232 | A1 | 12/2012 | Wolf et al. |
| 2013/0011332 | A1 | 1/2013 | Boyden et al. |
| 2013/0184695 | A1 | 7/2013 | Fourkas et al. |
| 2013/0190744 | A1 | 7/2013 | Avram et al. |
| 2013/0324989 | A1 | 12/2013 | Leung et al. |
| 2014/0200511 | A1 | 7/2014 | Boyden et al. |
| 2014/0303697 | A1 | 10/2014 | Anderson et al. |
| 2016/0151200 | A1 | 6/2016 | Kammer et al. |
| 2016/0175141 | A1 | 6/2016 | Wu et al. |
| 2017/0274011 | A1 | 9/2017 | Garibyan et al. |
| 2017/0274078 | A1 | 9/2017 | Garibyan et al. |
| 2018/0250056 | A1 | 9/2018 | Avram et al. |
| 2019/0053939 | A1 | 2/2019 | Garibyan et al. |
| 2019/0183558 | A1 | 6/2019 | Anderson et al. |
| 2019/0192424 | A1 | 6/2019 | Garibyan et al. |
| 2021/0244817 | A1 | 8/2021 | Garibyan et al. |

FOREIGN PATENT DOCUMENTS

| | | |
|---|---|---|
| JP | 2003-534366 A | 11/2003 |
| JP | 06-510758 A | 3/2006 |
| JP | 2010/508130 A | 3/2010 |
| JP | 2011-516168 A | 5/2011 |
| WO | WO 90/03795 A1 | 4/1990 |
| WO | WO 93/00930 A1 | 1/1993 |
| WO | WO 2001/05372 A2 | 1/2001 |
| WO | WO 01/91720 A2 | 12/2001 |
| WO | WO 03/078596 A2 | 9/2003 |
| WO | WO 2008/015380 A2 | 2/2008 |
| WO | WO 2008/055243 A2 | 5/2008 |
| WO | WO 2009/009540 A1 | 1/2009 |
| WO | WO 2009/047362 A2 | 4/2009 |
| WO | WO 2009/102367 A2 | 8/2009 |
| WO | WO 2009/146053 A1 | 12/2009 |
| WO | WO 2013/059133 A1 | 4/2013 |
| WO | WO 2015/019257 A1 | 2/2015 |

OTHER PUBLICATIONS

International Search Report and Written Opinion dated Apr. 12, 2011 for Application No. PCT/US2011/024766.
International Preliminary Report on Patentability dated Aug. 30, 2012 for Application No. PCT/US2011/024766.
International Search Report and Written Opinion for International Application No. PCT/US2020/043280 dated Nov. 9, 2020.
International Search Report and Written Opinion for International Application No. PCT/US2015/047292 dated Dec. 7, 2015.
International Preliminary Report on Patentability dated Mar. 9, 2017 for Application No. PCT/US2015/047292.
Partial European Search Report dated Mar. 22, 2018 for Application No. EP 15836780.5.
Extended European Search Report dated Jun. 26, 2018 for Application No. EP 15836780.5.
International Search Report and Written Opinion for International Application No. PCT/US2015/047301 dated Dec. 14, 2015.
International Preliminary Report on Patentability dated Mar. 9, 2017 for Application No. PCT/US2015/047301.
Partial European Search Report dated Mar. 24, 2020, for Application No. EP 17847238.6.
Extended European Search Report dated Dec. 7, 2020 for Application No. EP 17847328.6.
International Search Report and Written Opinion dated Nov. 3, 2017 for Application No. PCT/US2017/048995.
International Preliminary Report on Patentability dated Mar. 14, 2019 for Application No. PCT/US2017/048995.
Extended European Search Report dated Aug. 16, 2019 for Application No. EP 17757262.5.
International Search Report and Written Opinion dated May 15, 2017 for Application No. PCT/US2017/019268.
International Preliminary Report on Patentability dated Sep. 7, 2018 for Application No. PCT/US2017/019268.
[No Author Listed], Isotonic (https://biologydictionary.net/isotonic/) accessed Jun. 21, 2018, pp. 1-4 (Year: 2018).
[No Author Listed], Polysorbate-20 (https://web.archive.org/web/20130315082056/http://www.ewg.org:80/skindeep/ingredient/705137/POLYSORBATE-20/) available Mar. 15, 2013, pp. 1-3 (Year: 2013).
[No Author Listed], World Fine Chemicals Handbook. Institute of Science and Technology Information, Ministry of Chemical Industry, Ed. May 3, 19861;187-90.
[No Author Listed], Mosby's Dictionary of Medicine, Nursing & Health Professions. 8th Edition. Myers, Ed. Mosby Elsevier. St Louis, MO. 2009. 1 page.
Abbott et al., Front. Pharmacol. Conference Abstract: Structure and function of the blood-brain barrier. Pharmacology and Toxicology of the Blood-Brain Barrier: State of the Art, Needs for Future Research and Expected Benefits for the EU. Feb. 11-12, 2010. (doi:10.3389/conf.fphar.2010.02.00002).
Armitage et al., Toxic and osmotic effects of glycerol on human granulocytes. Am J Physiol. Nov. 1984;247(5 Pt 1):C382-9. doi: 10.1152/ajpcell.1984.247.5.C382.
Ash, Chronic peritoneal dialysis catheters: overview of design, placement, and removal procedures. Semin Dial. Jul.-Aug. 2003;16(4):323-34.
Ballabh et al., The blood-brain barrier: an overview: structure, regulation, and clinical implications. Neurobiol Dis. Jun. 2004;16(1):1-13. doi: 10.1016/j.nbd.2003.12.016.
Barnard, The effects of extreme cold on sensory nerves. Ann R Coll Surg Engl. May 1980;62(3):180-7.
Brink et al., Abdominoplasty with direct resection of deep fat. Plast Reconstr Surg. May 2009; 123(5):1597-603. doi: 10.1097/PRS.0b013e3181a07708.
Calandria, Cryoanalgesia for post-herpetic neuralgia: a new treatment. Int J Dermatol. Jun. 2011;50(6):746-50. doi: 10.1111/j.1365-4632.2010.04792.x.
Ding et al., Association between non-subcutaneous adiposity and calcified coronary plaque: a substudy of the Multi-Ethnic Study of Atherosclerosis. Am J Clin Nutr. Sep. 2008;88(3):645-50.
Dogan et al., Microstructural Control of Complex-Shaped Ceramics Processed by Freeze Casting. CFI Ceramic Forum International. May 2002;79(5);E35(1-4).

(56) References Cited

OTHER PUBLICATIONS

Dua et al., Liposome: Methods of Preparation and Applications. Int J. Pharm Stud Res. Apr. 2012; 3(2): 14-20.
Fox et al., Abdominal visceral and subcutaneous adipose tissue compartments: association with metabolic risk factors in the Framingham Heart Study. Circulation. Jul. 3, 2007;116(1):39-48. Epub Jun. 18, 2007.
Fruhstorfer et al., The effects of thermal stimulation on clinical and experimental itch. Pain. Feb. 1986;24(2):259-69.
Gage et al., Experimental cryosurgery investigations in vivo. Cryobiology. Dec. 2009;59(3):229-43. doi: 10.1016/j.cryobiol.2009.10.001. Epub Oct. 13, 2009.
Garaulet et al., Relationship between fat cell size and number and fatty acid composition in adipose tissue from different fat depots in overweight/obese humans. Int J Obes (Lond). Jun. 2006;30(6):899-905.
Garbay et al., Myelin synthesis in the peripheral nervous system. Prog Neurobiol. Jun. 2000;61(3):267-304.
Garibyan et al., Neural Selective Cryoneurolysis with Ice Slurry Injection in a Rat Model. Anesthesiology. Jul. 2020; 133(1):185-194. doi: 10.1097/ALN.0000000000003124.
Garibyan et al., Subcutaneous Fat Reduction with Injected Ice Slurry. Plast Reconstr Surg. Apr. 2020; 145(4):725e-733e. doi: 10.1097/PRS.0000000000006658.
Ge et al., Calculations of Freezing Point Depression, Boiling Point Elevation, Vapor Pressure and Enthalpies of Vaporization of Electrolyte Solutions by a Modified Three-Characteristic Parameter Correlation Model. J Sol Chem. Jul. 9, 2009;38(9):1097-17.
Ge et al., Estimation of Freezing Point Depression, Boiling Point Elevation, and Vaporization Enthalpies of Electrolyte Solutions. Ind Eng Chem Res. Jan. 15, 2009;48(4):2229-35.
Gradinger et al., Abdominoplasty. The Art of Aesthetic Surgery: Principles and Techniques. Foad Nahai ed., 1st Ed. 2005. 74 pages.
Hackel et al., Transient opening of the perineurial barrier for analgesic drug delivery. Proc Natl Acad Sci U S A. Jul. 17, 2012;109(29):E2018-27. doi: 10.1073/pnas.1120800109. Epub Jun. 25, 2012.
Halkier-Sorensen et al., The relevance of low skin temperature inhibiting histamine-induced itch to the location of contact urticarial symptoms in the fish processing industry. Contact Dermatitis. Sep. 1989;21(3):179-83.
Han et al., Efficacy and safety of high concentration lidocaine for trigeminal nerve block in patients with trigeminal neuralgia. Int J Clin Pract. Feb. 2008;62(2):248-54. Epub Nov. 23, 2007. (Abstract Only).
Hargreaves et al., A new and sensitive method for measuring thermal nociception in cutaneous hyperalgesia. Pain. Jan. 1988;32(1):77-88.
Hirakawa et al., Loss and recovery of the blood-nerve barrier in the rat sciatic nerve after crush injury are associated with expression of intercellular junctional proteins. Exp Cell Res. Apr. 1, 2003;284(2):196-210. doi: 10.1016/s0014-4827(02)00035-6.
Kasza et al., Medical Ice Slurry Coolants for Inducing Targeted-Organ/Tissue Protective Cooling. Argonne National Labratory. Jun. 2008. 9 pages.
Kauffeld et al., Ice Slurry Applications. Int J Refrig. Dec. 1, 2010;33(8):1491-1505.
Langert et al., Strategies for Targeted Delivery to the Peripheral Nerve. Front Neurosci. Nov. 27, 2018;12:887. doi: 10.3389/fnins.2018.00887. eCollection 2018.
Lampe et al., Rapid Induction of Heterogeneous Ice Nucleation in a Biologically Compatible Coolant. Int J Transp Phenom. 2011;12(3-4):307-317.
Laverson, Improving abdominoplasty results: reconstruction of the linea alba sulcus by direct fat excision. Aesthet Surg J. Nov.-Dec. 2006;26(6):682-6. doi: 10.1016/j.asj.2006.10.016.
Lenz et al., The freezing threshold of the peripheral motor nerve: an electrophysiological and light-microscopical study on the sciatic nerve of the rabbit. Cryobiology. Oct. 1975; 12(5):486-96.
Levin et al., A pilot study of ice-slurry application for inducing laparoscopic renal hypothermia. BJU Int. Jan. 2007;99(1):166-70. Epub Nov. 10, 2006.
Li et al., Changes in the blood-nerve barrier after sciatic nerve cold injury: indications supporting early treatment. Neural Regen Res. Mar. 2015; 10(3): 419-424. doi: 10.4103/1673-5374.153690: 10.4103/1673-5374.153690.
Mitchell et al., Degeneration of non-myelinated axons in the rat sciatic nerve following lysolecithin injection. Acta Neuropathol. 1982;56(3):187-93.
Modak et al., Agglomeration Control of Ice Particles in Ice-Water Slurry System Using Surfactant Additives. HVAC&R Res. 2002;8(4):453-66.
Oku et al., A simple procedure for the determination of the trapped vol. of liposomes. Biochim Biophys Acta. Oct. 7, 1982; 691(2): 332-340.
Peltonen et al., Barriers of the peripheral nerve. Tissue Barriers. Jul. 1, 2013;1(3):e24956. doi: 10.4161/tisb.24956. Epub May 30, 2013.
Pradel et al., Cryosurgical treatment of genuine trigeminal neuralgia. Br J Oral Maxillofac Surg. Jun. 2002;40(3):244-7.
Pramanick et al., Excipient Selection in Parenteral Formulation Development. Pharma Times. Mar. 2013;45(3):65-77.
Rathmell et al., Chapter 14—Intercostal Nerve Block and Neurolysis. Atlas of Image-Guided Intervention in Regional Anesthesia and Pain Medicine. 2012. p. 201-3.
Rengachary et al., Effect of glycerol on peripheral nerve: an experimental study. Neurosurgery. Dec. 1983;13(6):681-8. doi: 10.1227/00006123-198312000-00012.
Richner et al., Functional and Structural Changes of the Blood-Nerve-Barrier in Diabetic Neuropathy. Front Neurosci. Jan. 14, 2019;12:1038. doi: 10.3389/fnins.2018.01038. eCollection 2018.
Santamaria et al., Tetrodotoxin, epinephrine, and chemical permeation enhancer combinations in peripheral nerve blockade. Anesth Analg. Jun. 2017; 124(6):1804-1812. doi: 10.1213/ANE.0000000000002072.
Shikanov et al., Microparticulate ice slurry for renal hypothermia: laparoscopic partial nephrectomy in a porcine model. Urology. Oct. 2010; 76(4):1012-6. doi: 10.1016/j.urology.2009.12.066. Epub Mar. 31, 2010.
Sugiritama, Histology of Nervous System. Educational Staff at Medical Faculty of Udayana University. Published Jun. 23, 2009 (available at https://www.slideshare.net/sugiritama/histologic-structure-of-nervous-system).
Suzuki et al., Particle Size Depression and Drag Reduction of Ice Slurry Treated with Combination Additives of Surfactants and Poly(vinyl alcohol). J Chem Eng Jap. 2010;43(6):482-6.
Van Eps et al., Distal limb cryotherapy for the prevention of acute laminitis. Clin Tech Equine Pract. Mar. 1, 2004;3(1):64-70.
Vanden Hoek et al., Induced hypothermia by central venous infusion: saline ice slurry versus chilled saline. Crit Care Med. Sep. 2004;32(9 Suppl):S425-31.
Yamamoto et al., Adipose depots possess unique developmental gene signatures. Obesity (Silver Spring). May 2010;18(5):872-878. doi: 10.1038/oby.2009.512. Epub Jan. 28, 2010. Erratum in:Obesity (Silver Spring). May 2010; 18(5):1064.
Yang et al., Getting Drugs across Biological Barriers. Adv Mater. Oct. 2017;29(37):10.1002/adma.201606596. doi: 10.1002/adma.201606596. Epub Jul. 28, 2017.
Yao et al., Medical Polymer Materials. Chemical Industry Press. Apr. 30, 2008;908-10.
U.S. Appl. No. 15/505,038, filed Feb. 17, 2017, Garibyan et al.
U.S. Appl. No. 15/505,042, filed Feb. 17, 2017, Garibyan et al.
U.S. Appl. No. 17/188,359, filed Mar. 1, 2021, Garibyan et al.
U.S. Appl. No. 16/288,073, filed Feb. 27, 2019, Garibyan et al.
U.S. Appl. No. 16/327,266, filed Feb. 21, 2019, Anderson et al.
U.S. Appl. No. 16/080,092, filed Aug. 27, 2018, Garibyan et al.
PCT/US2011/024766, Apr. 12, 2011, International Search Report and Written Opinion.
PCT/US2011/024766, Aug. 30, 2012, International Preliminary Report on Patentability.
PCT/US2020/043280, Nov. 9, 2020, International Search Report and Written Opinion.

(56) References Cited

OTHER PUBLICATIONS

U.S. Appl. No. PCT/US2015/047292, Dec. 7, 2015, International Search Report and Written Opinion.
PCT/US2015/047292, Mar. 9, 2017, International Preliminary Report on Patentability.
EP 15836780.5, Mar. 22, 2018, Partial European Search Report.
EP 15836780.5, Jun. 26, 2018, Extended European Search Report.
PCT/US2015/047301, Dec. 14, 2015, International Search Report and Written Opinion.
PCT/US2015/047301, Mar. 9, 2017, International Preliminary Report on Patentability.
EP 17847238.6, Mar. 24, 2020, Partial European Search Report.
EP 17847238.6, Dec. 7, 2020, Extended European Search Report.
PCT/US2017/048995, Nov. 3, 2017, International Search Report and Written Opinion.
PCT/US2017/048995, Mar. 14, 2019, International Preliminary Report on Patentability.
EP 17757262.5, Aug. 16, 2019, Extended European Search Report.
PCT/US2017/019268, May 15, 2017, International Search Report and Written Opinion.
PCT/US2017/019268, Sep. 7, 2018, International Preliminary Report on Patentability.
International Search Report and Written Opinion for International Application No. PCT/US2021/014789 dated May 18, 2021.
Amasheh et al., Claudin-2 expression induces cation-selective channels in tight junctions of epithelial cells. J Cell Sci. Dec. 15, 2002;115(Pt 24):4969-76. doi: 10.1242/jcs.00165.
Antonijevic et al., Perineurial defect and peripheral opioid analgesia in inflammation. J Neurosci. Jan. 1995;15(1 Pt 1):165-72. doi: 10.1523/JNEUROSCI.15-01-00165.1995.
Begley, Delivery of therapeutic agents to the central nervous system: the problems and the possibilities. Pharmacol Ther. Oct. 2004; 104(1):29-45. doi: 10.1016/j.pharmthera.2004.08.001.
Binshtok et al., Inhibition of nociceptors by TRPV1-mediated entry of impermeant sodium channel blockers. Nature. Oct. 4, 2007;449(7162):607-10. doi: 10.1038/nature06191.
Blasig et al., Occludin protein family: oxidative stress and reducing conditions. Antioxid Redox Signal. Sep. 1, 2011;15(5):1195-219. doi: 10.1089/ars.2010.3542. Epub May 5, 2011.
Blasig et al., On the self-association potential of transmembrane tight junction proteins. Cell Mol Life Sci. Feb. 2006;63(4):505-14. doi: 10.1007/s00018-005-5472-x.
Colegio et al., Claudin extracellular domains determine paracellular charge selectivity and resistance but not tight junction fibril architecture. Am J Physiol Cell Physiol. Jun. 2003;284(6):C1346-54. doi: 10.1152/ajpcell.00547.2002. Epub Apr. 16, 2003.
Coyne et al., Role of claudin interactions in airway tight junctional permeability. Am J Physiol Lung Cell Mol Physiol. Nov. 2003;285(5):L1166-78. doi: 10.1152/ajplung.00182.2003. Epub Aug. 8, 2003.
Cukierman et al., Residues in a highly conserved claudin-1 motif are required for hepatitis C virus entry and mediate the formation of cell-cell contacts. J Virol. Jun. 2009;83(11):5477-84. doi: 10.1128/JVI.02262-08. Epub Mar. 18, 2009.
Cuschieri et al., Hypertonic preconditioning inhibits macrophage responsiveness to endotoxin. J Immunol. Feb. 1, 2002;168(3):1389-96. doi: 10.4049/jimmunol.168.3.1389.
Fried et al., Peginterferon alfa-2a plus ribavirin for chronic hepatitis C virus infection. N Engl J Med. Sep. 26, 2002;347(13):975-82. doi: 10.1056/NEJMoa020047.
Fujita et al., Clostridium perfringens enterotoxin binds to the second extracellular loop of claudin-3, a tight junction integral membrane protein. FEBS Lett. Jul. 7, 2000;476(3):258-61. doi: 10.1016/s0014-5793(00)01744-0.
Fujita et al., Permeability characteristics of tetragastrins across intestinal membranes using the Caco-2 monolayer system: comparison between acylation and application of protease inhibitors. Pharm Res. Sep. 1998; 15(9):1387-92. doi: 10.1023/a:1011997404306.
Furuse et al., Claudin-based tight junctions are crucial for the mammalian epidermal barrier: a lesson from claudin-1-deficient mice. J Cell Biol. Mar. 18, 2002;156(6):1099-111. doi: 10.1083/jcb.200110122. Epub Mar. 11, 2002.
Furuse et al., Occludin: a novel integral membrane protein localizing at tight junctions. J Cell Biol. Dec. 1993; 123(6 Pt 2): 1777-88. doi: 10.1083/jcb.123.6.1777.
Furuse et al., A single gene product, claudin-1 or -2, reconstitutes tight junction strands and recruits occludin in fibroblasts. J Cell Biol. Oct. 19, 1998;143(2):391-401. doi: 10.1083/jcb.143.2.391.
Graham et al., Characteristics of a human cell line transformed by DNA from human adenovirus type 5. J Gen Virol. Jul. 1977;36(1):59-74. doi: 10.1099/0022-1317-36-1-59.
Grant et al., Perineural antinociceptive effect of opioids in a rat model. Acta Anaesthesiol Scand. Aug. 2001;45(7):906-10. doi: 10.1034/j.1399-6576.2001.045007906.x.
Hamamoto et al., Antimicrobial activity and stability to proteolysis of small linear cationic peptides with D-amino acid substitutions. Microbiol Immunol. 2002;46(11):741-9. doi: 10.1111/j.1348-0421.2002.tb02759.x.
Ikenouchi et al., Tricellulin constitutes a novel barrier at tricellular contacts of epithelial cells. J Cell Biol. Dec. 19, 2005;171(6):939-45. doi: 10.1083/jcb.200510043.
Junger et al., Hypertonicity regulates the function of human neutrophils by modulating chemoattractant receptor signaling and activating mitogen-activated protein kinase p38. J Clin Invest. Jun. 15, 1998;101(12):2768-79. doi: 10.1172/JCI1354.
Kanda et al., Chronic inflammatory demyelinating polyneuropathy: decreased claudin-5 and relocated ZO-1. J Neurol Neurosurg Psychiatry. May 2004; 75(5):765-9. doi: 10.1136/jnnp.2003.025692.
Kondoh et al., A novel strategy for the enhancement of drug absorption using a claudin modulator. Mol Pharmacol. Mar. 2005;67(3):749-56. doi: 10.1124/mol.104.008375. Epub Dec. 15, 2004.
Krause et al., Structure and function of claudins. Biochim Biophys Acta. Mar. 2008; 1778(3):631-45. doi: 10.1016/j.bbamem.2007.10.018. Epub Oct. 25, 2007.
Kucenas et al., CNS-derived glia ensheath peripheral nerves and mediate motor root development. Nat Neurosci. Feb. 2008;11(2):143-51. doi: 10.1038/nn2025. Epub Jan. 6, 2008.
Labuz et al., Immune cell-derived opioids protect against neuropathic pain in mice. J Clin Invest. Feb. 2009;119(2):278-86. doi: 10.1172/JCI36246. Epub Jan. 12, 2009.
Manns et al., Peginterferon alfa-2b plus ribavirin compared with interferon alfa-2b plus ribavirin for initial treatment of chronic hepatitis C: a randomised trial. Lancet. Sep. 22, 2001;358(9286):958-65. doi: 10.1016/s0140-6736(01)06102-5.
Marsland et al., Cryogenic damage to peripheral nerves and blood vessels in the rat. Br J Anaesth. Jun. 1983;55(6):555-8. doi: 10.1093/bja/55.6.555.
Morita et al., Claudin multigene family encoding four-transmembrane domain protein components of tight junction strands. Proc Natl Acad Sci U S A. Jan. 19, 1999;96(2):511-6. doi: 10.1073/pnas.96.2.511.
Mrsny et al., A key claudin extracellular loop domain is critical for epithelial barrier integrity. Am J Pathol. Apr. 2008;172(4):905-15. doi: 10.2353/ajpath.2008.070698. Epub Mar. 18, 2008.
Ohki et al., Interaction of melittin with lipid membranes. Biochim Biophys Acta. Sep. 14, 1994;1194(2):223-32. doi: 10.1016/0005-2736(94)90303-4.
Piña-Oviedo et al., The normal and neoplastic perineurium: a review. Adv Anat Pathol. May 2008; 15(3):147-64. doi: 10.1097/PAP.0b013e31816f8519.
Pummi et al., Tight junction proteins ZO-1, occludin, and claudins in developing and adult human perineurium. J Histochem Cytochem. Aug. 2004;52(8):1037-46. doi: 10.1369/jhc.3A6217.2004.
Rousset et al., Presence and cell growth-related variations of glycogen in human colorectal adenocarcinoma cell lines in culture. Cancer Res. Feb. 1979; 39(2 Pt 1):531-4.
Sagie et al., Prolonged sensory-selective nerve blockade. Proc Natl Acad Sci U S A. Feb. 23, 2010;107(8):3740-5. doi: 10.1073/pnas.0911542107. Epub Feb. 4, 2010.
Simons et al., Effect of chemical permeation enhancers on nerve blockade. Mol Pharm. Jan.-Feb. 2009;6(1):265-73. doi: 10.1021/mp800167a.

(56) References Cited

OTHER PUBLICATIONS

Sonoda et al., Clostridium perfringens enterotoxin fragment removes specific claudins from tight junction strands: Evidence for direct involvement of claudins in tight junction barrier. J Cell Biol. Oct. 4, 1999;147(1):195-204. doi: 10.1083/jcb.147.1.195.

Stein et al., Intrinsic mechanisms of antinociception in inflammation: local opioid receptors and beta-endorphin. J Neurosci. Apr. 1990; 10(4):1292-8. doi: 10.1523/JNEUROSCI.10-04-01292.1990.

Takahashi et al., Role of C-terminal regions of the C-terminal fragment of Clostridium perfringens enterotoxin in its interaction with claudin-4. Control Release. Nov. 2, 2005;108(1):56-62. doi: 10.1016/j.jconrel.2005.07.008. Epub Aug. 8, 2005.

Todd et al., Ionic permeability of the frog sciatic nerve perineurium: parallel studies of potassium and lanthanum penetration using electrophysiological and electron microscopic techniques. J Neurocytol. Aug. 2000;29(8):551-67. doi: 10.1023/a:1011015916768.

Vietor et al., Perturbation of the tight junction permeability barrier by occludin loop peptides activates beta-catenin/TCF/LEF-mediated transcription. EMBO Rep. Apr. 2001;2(4):306-12. doi: 10.1093/embo-reports/kve066.

Weerasuriya et al., Modification of permeability of frog perineurium to [14C]-sucrose by stretch and hypertonicity. Brain Res. Sep. 21, 1979;173(3):503-12. doi: 10.1016/0006-8993(79)90244-0.

Wen et al., Selective decrease in paracellular conductance of tight junctions: role of the first extracellular domain of claudin-5. Mol Cell Biol. Oct. 2004;24(19):8408-17. doi: 10.1128/MCB.24.19.8408-8417.2004.

Winkler et al., Molecular determinants of the interaction between Clostridium perfringens enterotoxin fragments and claudin-3. J Biol Chem. Jul. 10, 2009;284(28):18863-72. doi: 10.1074/jbc.M109.008623. Epub May 8, 2009.

Wong et al., A synthetic peptide corresponding to the extracellular domain of occludin perturbs the tight junction permeability barrier. J Cell Biol. Jan. 27, 1997;136(2):399-409. doi: 10.1083/jcb.136.2.399.

Wong et al., Targeted and reversible disruption of the blood-testis barrier by an FSH mutant-occludin peptide conjugate. FASEB J. Feb. 2007;21(2):438-48. doi: 10.1096/fj.05-4144com. Epub Dec. 13, 2006.

Wu et al., Identification of new claudin family members by a novel PSI-BLAST based approach with enhanced specificity. Proteins. Dec. 1, 2006;65(4):808-15. doi: 10.1002/prot.21218.

Zimmermann, Ethical guidelines for investigations of experimental pain in conscious animals. Pain. Jun. 1983; 16(2):109-110. doi: 10.1016/0304-3959(83)90201-4.

Zollner et al., Painful inflammation-induced increase in mu-opioid receptor binding and G-protein coupling in primary afferent neurons. Mol Pharmacol. Aug. 2003;64(2):202-10. doi: 10.1124/mol.64.2.202.

Zwanziger et al., A peptidomimetic tight junction modulator to improve regional analgesia. Mol Pharm. Jun. 4, 2012;9(6): 1785-94. doi: 10.1021/mp3000937. Epub May 10, 2012.

Conaway, Ice packs in diabetic neuropathy. Phys Ther Rev. Aug. 1961;41:586-8. doi: 10.1093/ptj/41.8.586. PMID: 13694966.

Carruthers et al., Cryolipolysis and skin tightening. Dermatol Surg. Dec. 2014;40 Suppl 12:S184-9. doi: 10.1097/DSS.0000000000000229.

Foster et al., Sympathetic but not sensory denervation stimulates white adipocyte proliferation. Am J Physiol Regul Integr Comp Physiol. Dec. 2006;291(6):R1630-7. doi: 10.1152/ajpregu.00197.2006. Epub Aug. 3, 2006.

Manasse et al., Myocardial acute and chronic histological modifications induced by cryoablation. Eur J Cardiothorac Surg. Mar. 2000;17(3):339-40. doi: 10.1016/s1010-7940(99)00361-9.

Segev et al., Endocardial cryotherapy as a novel strategy of improving myocardial perfusion in a patient with severe coronary artery disease. Catheter Cardiovasc Interv. Oct. 2003;60(2):229-32. doi: 10.1002/ccd.10621.

Stevens et al., Molecular and Histological Evidence Detailing Clinically Observed Skin Improvement Following Cryolipolysis. Aesthet Surg J. May 17, 2021;sjab226. doi: 10.1093/asj/sjab226. Online ahead of print.

Stevens, Does Cryolipolysis Lead to Skin Tightening? A First Report of Cryodermadstringo. Aesthet Surg J. Aug. 2014;34(6):NP32-4. doi: 10.1177/1090820X14539699. Epub Aug. 1, 2014.

Zelickson et al., Cryolipolysis for Noninvasive Fat Cell Destruction: Initial Results from a Pig Model. Dermatol Surg. Oct. 2009;35(10):1462-70. doi: 10.1111/j.1524-4725.2009.01259.x. Epub Jul. 13, 2009.

U.S. Appl. No. 17/535,493, filed Nov. 24, 2021, Garibyan et al.

EP 22189301.9, Apr. 12, 2023, Extended European Search Report.

Extended European Search Report for Application No. EP 22189301.9, dated Apr. 12, 2023.

* cited by examiner

COMPOSITIONS AND METHODS FOR TREATMENT OF NEUROLOGICAL DISORDERS

RELATED APPLICATIONS

This application is a continuation of U.S. patent application Ser. No. 15/505,039, filed Feb. 17, 2017, which is a national stage filing under 35 U.S.C. § 371 of international application number PCT/US2015/047292, filed Aug. 27, 2015, which claims priority under 35 U.S.C. § 119(e) to U.S. provisional application Ser. No. 62/042,979, filed Aug. 28, 2014, U.S. U.S. provisional application Ser. No. 62/121,329, filed Feb. 26, 2015, and U.S. provisional application Ser. No. 62/121,472, filed Feb. 26, 2015, are the entire contents of each of which are incorporated herein by reference.

BACKGROUND OF THE INVENTION

Chronic peripheral nerve pain is a common problem in the general population and, in particular, military veterans. It can arise from numerous causes, such as surgery, trauma, neuroma, metabolic or genetic disorder, infection or it can be idiopathic. It is estimated that 20-30% of all extremity injuries in the US military involve peripheral nerve damage. Severe peripheral nerve injury and amputation have devastating effects on quality of life due to intractable neuropathic pain. Treatment of refractory nerve pain has been attempted using oral pain medications, such as narcotics, nonsteroidal anti-inflammatory drugs (NSAIDs), surgical and various percutaneous procedures, including radiofrequency and alcohol ablation. However, there are numerous complications associated with these treatments, including addiction to narcotics and the need for multiple procedures. Overall, current treatment options for chronic peripheral nerve pain fail to provide satisfactory results.

Cryoneurolysis is the use of cold to target nerves. Cryoneurolysis is a specialized technique for providing long-term pain relief in interventional pain management settings. The application of cold to nerves creates a conduction block similar to the effect of local anesthetics and, if the nerve is frozen, leads to Wallerian degeneration of the nerve. Cryoneurolysis has been used for many years, albeit sparingly, for treatment of phantom limb pain, pain secondary to trigeminal neuralgia, post-thoracotomy chest wall pain, peripheral neuritis pain, post herpetic neuralgia pain. The technique involves a probe 1.4 to 2 millimeters in size that utilizes pressurized gas (e.g., nitrous oxide or carbon dioxide) at 600-800 psi to generate temperatures as cold as −89° C. or lower at the tip of the probe through adiabatic cooling under the Joule-Thompson effect, thereby forming an ice ball at the target area. The probe is placed directly on the nerve and any tissue that comes into contact with the probe is destroyed due to the extreme cold temperatures used. Because the surrounding tissue is almost always injured or damaged, this procedure is not selective. In addition, the damage to the nerves in these temperature ranges can be permanent.

Procedures involving cryoneurolysis that selectively target peripheral nerves without damaging the surrounding tissue and provide sustained treatment of pain would be highly desirable.

SUMMARY OF THE INVENTION

In one aspect, the invention provides a method of providing reversible inhibition of peripheral nerves to a subject in need thereof. The method comprises providing a biocompatible ice slurry to the peripheral nerves for a duration sufficient to inhibit the peripheral nerves in the subject, wherein the inhibition is reversible. In some embodiments, the inhibition is reversed after about 5 months or less. The peripheral nerves targeted for inhibition can be subcutaneous nerves; somatic nerves, including sensory nerves, motor nerves, cranial nerves or spinal nerves; and autonomic nerves, including sympathetic, parasympathetic or enteric nerves. In some embodiments, the biocompatible ice slurry is provided along the perineural sheath of a peripheral nerve.

In one embodiment, the biocompatible ice slurry comprises ice particles and a lactated Ringer's solution or a lactated electrolyte solution.

In another embodiment, the biocompatible ice slurry further comprises hetastarch or dextrose.

In yet another embodiment, the biocompatible ice slurry further comprises about 0.1% to about 20% glucose.

In yet another embodiment, the biocompatible ice slurry further comprises about 0.1% to about 20% glycerol.

In yet another embodiment, the biocompatible ice slurry further comprises about 0.1% to about 6% hetastarch.

In yet another embodiment, the biocompatible ice slurry comprises ice particles and saline.

In yet another embodiment, the biocompatible ice slurry further comprises about 0.1% to about 20% glycerol.

In yet another embodiment, the biocompatible ice slurry further comprises about 0.1% to about 20% dextrose.

In yet another embodiment, the biocompatible ice slurry further comprises about 0.1% to about 5% ethanol.

In yet another embodiment, the biocompatible ice slurry further comprises about 0.1% to about 10% poly vinyl alcohol.

In yet another embodiment, the biocompatible ice slurry further comprises at least one ion, sugar, polysaccharide, lipid, oil, lysolecithin, amino acid, caffeine, surfactant, antimetabolite or combinations thereof. The at least one ion includes, but is not limited to, calcium, potassium, hydrogen, chloride, magnesium, sodium, lactate, phosphate, zinc, sulfur, nitrate, ammonium, carbonate, hydroxide, iron, barium or combinations thereof, including salts thereof. The at least one sugar includes, but is not limited to, glucose, sorbitol, mannitol, hetastarch, sucrose, or combinations thereof. The at least one oil includes, but is not limited to, canola oil, coconut oil, corn oil, cottonseed oil, flaxseed oil, olive oil, palm oil, peanut oil, safflower oil, soybean oil, sunflower oil or combinations thereof.

In yet another embodiment, the surfactant is a detergent. The detergent includes, but is not limited to, deoxycholate, sodium tetradecyl sulphate, polidocanol, polysorbate (including polysorbate 20 (polyoxyethylen (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate)), sorbitan ester, poloxamater or combinations thereof.

In yet another embodiment, the biocompatible ice slurry comprises a peritoneal dialysis solution.

In yet another embodiment, the biocompatible ice slurry cools the nerves to between about 5° C. and about −40° C.

In yet another embodiment, the biocompatible ice slurry has a first equilibration temperature of between about 4° C. and about −30° C.

In yet another embodiment, the biocompatible ice slurry has a second equilibration temperature of between about 2° C. and about −30° C.

In yet another embodiment, the ice particles are spherical or round with a diameter of about 1 mm to about 0.01 mm.

In yet another embodiment, the biocompatible ice slurry further comprises an agent including, but not limited to, a vasoconstricting agent, corticosteroid, NSAID, anesthetic, glucocorticoid and a lipoxygenase inhibitor or combinations thereof. The vasoconstricting agent includes, but is not limited to, epinephrine or norepinephrine. The anesthetic includes, but is not limited to, lidocaine, bupivacaine, prilocaine, tetracaine, procaine, mepivicaine, QX-314 and etidocaine or combinations thereof.

In yet another embodiment, the biocompatible ice slurry is injected. The injection can be administered into or around any peripheral nerves including, but not limited to, the cutaneous nerve, trigeminal nerve, ilioinguinal nerve, intercostal nerve, interscalene nerve, intercostal nerves, supraclavicular nerve, infraclavicular nerve, axillary nerve, paravertebral nerve, transverse abdominis nerve, lumbar plexus nerve, femoral nerve, pudental, celiac plexus and sciatic nerve, any nerve conducting painful sensations or any injured nerve producing pain or disease.

In yet another embodiment, the biocompatible ice slurry is provided to the peripheral nerves of the subject by tumescent pumping of the slurry.

In yet another embodiment, pressure is applied at the site of injection to reduce blood flow.

In yet another embodiment, the tissue comprising the peripheral nerves is cooled externally prior to, during, or after providing the biocompatible ice slurry.

In yet another embodiment, ice content of the biocompatible ice slurry is monitored by ultrasound or imaging.

In yet another embodiment, the subject in need of treatment suffers from a disorder including, but not limited to, neuropathic pain, diabetic neuropathy pain, trigeminal neuralgia, post-herpetic neuralgia, phantom limb pain, cancer related itch or pain, burn itch or pain, lichen sclerosus, scalp itch, nostalgia parastethica, atopic dermatitis, eczema, psoriasis, lichen planus, vulvar itch, vulvodynia, lichen simplex chornicus, prurigo nodularis, itch mediated by sensory nerves, peripheral neuropathy, peripheral nerve damage, post-thoracotomy pain, incisional pain, chest pain, coccydynia, lower back pain (with or without radiculopathy), scars, neuromas, acute post-operation pain, lumbar facet joint syndrome and cutaneous pain disorder.

The cutaneous pain disorder includes, but is not limited to, reflex sympathetic dystrophy (RSD), phantom limb pain, neuroma, post herpetic neuralgia, headache, occipital neuralgia, tension headaches and vulvodynia.

In yet another embodiment, the subject in need of treatment suffers from a motor disorder including, but not limited to, hemifacial spasm, bladder spasm, laryngospasm and gustatory hyperhidrosis.

Other features and advantages of the invention will be apparent from the Detailed Description, and from the claims Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

DETAILED DESCRIPTION OF THE INVENTION

Definitions

Figure 1:
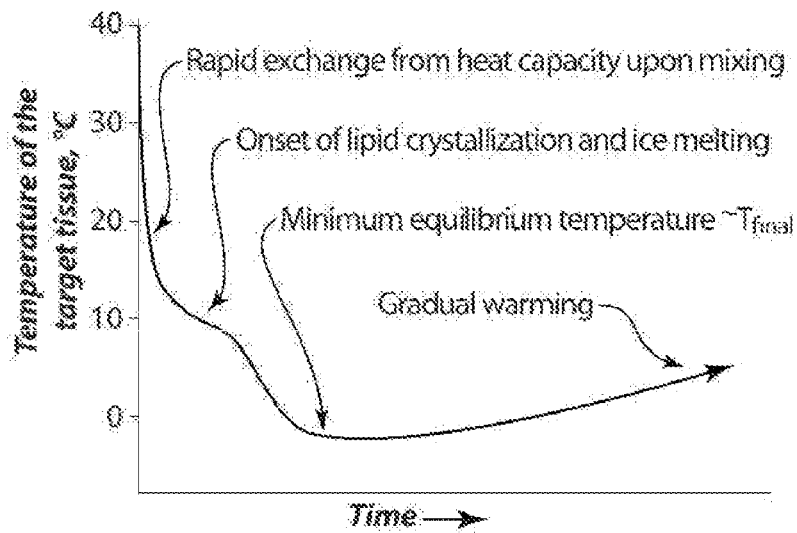
FIG. 1 depicts a quantitative model to illustrate the behavior of injected slurries.

Unless otherwise defined, all technical and scientific terms used herein have the same meaning as commonly understood those skilled in the art to which this invention pertains. In case of conflict, the present application, including definitions will control.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "biocompatible" refers to a substance or solution having the capability of coexistence with living tissues or organisms without causing harm.

As used herein, the term "ice" refers to the solid state of water (i.e., frozen water).

As used herein, the term "water" refers to $H_2O$ and all isotopes of $H_2O$, including $D_2O$, $T_2O$, etc., and mixtures thereof.

As used herein, the term "aqueous solution/aqueous slurry" refers to a solution/slurry containing $H_2O$ and all isotopes of $H_2O$, including $D_2O$, $T_2O$, etc., and mixtures thereof. Such solutions may include water in its solid, semi-solid and/or liquid states.

As used herein, the term "equilibrium" or "equilibrium temperature" refers to a temperature that is between the temperatures of a slurry and a tissue at the time of initial contact between the slurry and the tissue.

As used herein, "reversible inhibition" of peripheral nerves refers to a loss of function in the nerve which is recovered over time. Loss of function would include, for example, decreased thermal or mechanical sensation in the nerve.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

A "slurry" refers to solid phase particles (e.g., ice particles) suspended in a biocompatible liquid phase solution. The slurry may also contain gas phase bubbles.

A "subject" is a vertebrate, including any member of the class mammalia, including humans, domestic and farm animals, and zoo, sports or pet animals, such as, e.g., horse, cat, dog, mouse, rabbit, pig, sheep, goat, cattle and higher primates.

As used herein, the terms "treat," "treating," "treatment" and the like refer to reducing or ameliorating a disorder and/or symptoms associated therewith. It will be appreciated that, although not precluded, treating a disorder or condition does not require that the disorder, condition or symptoms associated therewith be completely eliminated.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods of the Invention

In one aspect, the invention involves introducing a composition comprising a cold slurry (e.g., ice slurry) into interstitial tissue, i.e., directly into the tissue rather than through a natural conduit of the body such as arteries, veins, or gut. When a volume of ice slurry is directly introduced into a volume of soft tissue, there is rapid heat exchange between the tissue and the slurry. When rapidly and locally injected, a pool of slurry is produced that mixes with a target volume of local tissue. By contrast, if a slurry is infused more slowly and with larger volume, the slurry penetrates and flows through spaces in the tissue, producing widespread channels filled with slurry in a process similar to the administration of tumescent anesthesia. With infusion, there can be sustained flow of slurry through tissue, especially tissue nearby the site of introduction. This tissue can be profoundly cooled to the temperature of the slurry itself, by the continuous or prolonged flow of slurry.

In general, there are two periods of heat exchange upon injection of slurry directly into tissue—a rapid equilibration between slurry and local tissue, followed by slower warming to body temperature. During the rapid equilibration, the slurry is warmed and the local tissue is cooled, until an equilibrium temperature is reached that is between the initial temperatures of the slurry and the tissue. During this rapid tissue cooling by heat exchange, three events occur: 1) heat stored by the heat capacity of the slurry and the tissue is exchanged; 2) heat released by the crystallization of tissue lipids is exchanged; and 3) heat absorbed by melting of slurry ice is exchanged. Some or all of the ice in the slurry melts, and some or all of the lipids in the tissue are crystallized, according to the parameters of the tissue and the slurry. Crystallization of lipids in the myelin sheath of nerves, or direct cooling of non-myelinated nerves, causes a targeted relief of pain.

After the rapid heat exchange with the slurry, there is gradual warming by heat exchange with the body. Gradual warming occurs by a combination of heat diffusion from surrounding warm tissue and by convective heating from blood flow. Blood flow can be reduced in the local tissue by pressure or by drugs, e.g., blood flow can be stopped or greatly reduced by applying pressure to the cold tissue or by addition of epinephrine or other vasoconstrictor agent(s) to the slurry. The desired level of pain relief may depend on temperature, rate of cooling, duration of cooling and the number of cooling cycles.

Effectiveness of treatment is related to the amount of lipid crystallization, amount and number of epidermal nerve fiber and dermal myelinated nerve fiber reduction, the minimum temperature achieved, the duration of cold temperatures, and the number of cold cycles (slurry injections can be easily repeated in one treatment session). All of these parameters can be controlled in a local tissue volume, by varying the amount and rate of introduction, of slurries containing various fractions of ice content.

I. Formulations

Through selection of slurry components, including liquid and cooled particle content (e.g., ice content), and application parameters, including placement, rate and volume of infusion, predictable target tissue cooling can be attained. During melting of the ice component of a slurry, the temperature of the slurry is at or near the melting point, keeping the slurry cold during and after infusion into tissue. Depending on the composition and osmolality of its liquid component, this melting temperature can be chosen for desired effects on the tissue, over a range from about −30 to about 10° C., in particular, over a range from about −30° C. to about 4° C., more in particular, over a range from about −30° C. and to about 2° C.

The temperature of the solution comprising the slurry can be adjusted by selection of liquid phase components, including various solvents and solutes and ions that produce a controlled freezing point depression (e.g., including aqueous solutions of NaCl and other biocompatible salts, other electrolytes such as potassium or chloride, glycerol, sugars, polysaccharides, lipids, surfactants, anti-metabolites and detergents).

The solution comprising the slurry can include, or consist essentially of, a lactated Ringer's solution or a saline solution or hetastarch solution. Slurry formulations can be made with dextrose, mannitol, glucose, sorbitol, mannitol, hetastarch, sucrose, glycerol or ethanol or poly vinyl alcohol. Freezing point depression to about −40° C. can be achieved with saline, glycerol, glucose, sorbitol, or mixtures thereof. In specific embodiments, slurry formulations can be made with about 0.1% to about 5% ethanol or about 0.1% to about 20% glycerol (e.g., in particular, about 5% to about 10% glycerol).

In specific embodiments, the solution comprising the slurry-comprises a lactated Ringer's solution with or without about 0.1% to about 20% glucose or glycerol; saline with or without about 0.1% to about 20% dextrose or glycerol; or a lactated Ringer's solution in 6% hetastarch. In another specific embodiment, the solution comprising the slurry can include about 0.1% to about 6% hetastarch in a lactated electrolyte solution.

Glycerol is desirable for cryoprotection and/or use as a surfactant. Freezing point depressions for glycerol-water solutions can be achieved as described below in Table 1.

TABLE 1

Freezing Points of Glycerol-Water Solutions

| Glycerol by Wt. (%) | Water (%) | Freezing Points (° C.) | Freezing Points (° F.) |
|---|---|---|---|
| 10.0 | 100.0 | 0.0 | 32.0 |
| 5.0 | 95.0 | −0.6 | 30.9 |
| 10.0 | 90.0 | −1.6 | 29.1 |
| 11.5[1] | 88.5 | −2.0 | 28.4 |
| 15.0 | 85.0 | −3.1 | 26.4 |
| 20.0 | 80.0 | −4.8 | 23.4 |
| 22.6[1] | 77.4 | −6.0 | 21.2 |
| 25.0 | 75.0 | −7.0 | 19.4 |
| 30.0 | 70.0 | −9.5 | 14.9 |
| 33.3[1] | 67.0 | −11.0 | 12.2 |
| 35.0 | 65.0 | −12.2 | 10.0 |
| 40.0 | 60.0 | −15.4 | 4.3 |
| 44.5[1] | 55.5 | −18.5 | −1.3 |
| 45.0 | 55.0 | −18.8 | −1.8 |
| 50.0 | 50.0 | −23.0 | −9.4 |
| 53.0[1] | 47.0 | −26.0 | −14.8 |
| 55.0 | 45.0 | −28.2 | −18.8 |
| 60.0 | 40.0 | −34.7 | −30.5 |
| 60.4[1] | 39.6 | −35.0 | −31.0 |
| 64.0[1] | 36.0 | −41.5 | −42.7 |
| 64.7[1] | 35.3 | −42.5 | −44.5 |
| 65.0 | 35.0 | −43.0 | −45.4 |
| 65.6[1] | 34.4 | −44.5 | −48.1 |
| 66.0[1] | 34.0 | −44.7 | −48.5 |
| 66.7[1] | 33.3 | −46.5 | −51.7 |
| 67.1[1] | 32.9 | −45.5 | −49.9 |
| 67.3[1] | 32.7 | −44.5 | −48.1 |
| 68.0[1] | 32.0 | −44.0 | −47.2 |
| 70.0 | 30.0 | −38.9 | −38.0 |
| 70.9[1] | 29.1 | −37.5 | −35.5 |
| 75.0 | 25.0 | −29.8 | −21.6 |
| 75.4[1] | 24.6 | −28.5 | −19.3 |
| 79.0[1] | 21.0 | −22.0 | −7.6 |
| 80.0 | 20.0 | −20.3 | −4.5 |
| 84.8[1] | 15.2 | −10.5 | 13.1 |
| 85.0 | 15.0 | −10.9 | 12.4 |
| 90.0 | 10.0 | −1.6 | 29.1 |
| 90.3[1] | 9.7 | −1.0 | 30.2 |
| 95.0 | 5.0 | 7.7 | 45.9 |
| 95.3[1] | 4.7 | 7.5 | 45.5 |
| 98.2[1] | 1.8 | 13.5 | 56.3 |
| 100.0 | 0.0 | 17.0 | 62.6 |

[1]denotes actual determinations. The remaining values were interpolated from the curve.

Ions that can be included in the slurry to produce a controlled freezing point depression include, but are not limited to calcium, potassium, hydrogen, chloride, magnesium, sodium, lactate, phosphate, zinc, sulfur, nitrate, ammonium, carbonate, hydroxide, iron, barium or combinations thereof, including salts formed thereof.

Local blood flow is an important factor, e.g., if a long treatment time is desired, agents that limit or eliminate local blood flow can be employed. The solution comprising the slurry can include vasoconstricting agents that reduce local tissue blood flow. Suitable vasoconstricting agents include, but are not limited to, epinephrine (e.g., 1/10,000 or less) and norepinephrine. Blood flow can also be decreased by use of tourniquet, pressure/compression, and suction of the area to be treated. Vasoconstriction can also be achieved by pre-cooling the tissue to be treated with topical application of cold in a form of Peltier cooling or application of ice or cold pack to the surface of the skin.

Addition of physiologically compatible surfactant molecules can enhance flow and tissue effects. Surfactants can also act as foaming agents. Suitable surfactant molecules include, but are not limited to, sodium tetradecyl sulphate, polysorbate, polysorbate 20 (polyoxyethylen (20) sorbitan monolaurate), polyoxyethylene sorbitan monooleate, sorbitan monooleate polyoxyethylene sorbitan monolaurate, lecithin, and polyoxyethylene-polyoxypropylene copolymers, polysorbate, polysorbate 20 (polyoxyethylen (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), sorbitan ester, poloxamater or combinations thereof.

Addition of agents such as lysolecithin, deoxycholate, or other surfactants or detergent to the slurry will allow targeting of non-myelinated nerves. For example, lysolecithin is known to cause reversible degeneration of non-myelinated axons (Mitchell J. Degeneration of Non-myelinated Axons in the Rat Sciatic Nerve Following Lysolecithin Injection. Acta Neuropathol (Berl) (1982) 56:187-193). This combination will allow targeting of myelinated and non-myelinated nerve fibers through slurry injection and thus lead to complete nerve block.

Accordingly, the solution comprising the slurry can include detergents that can function as freezing point depressants or agents to dissolve myelin sheaths. Such detergents include, but are not limited to, TWEEN® polysorbates, deoxycholate, cholate, phosphatidyl choline and sodium deoxycholate. Exemplary slurry formulations are shown in Table 2.

TABLE 2

Exemplary Slurry Formulations

| Slurry Composition | Temp |
|---|---|
| Normal Saline + 5% Dextrose + 5% Glycerol | −3.9 C. |
| Normal Saline + 5% Dextrose + 5% Glycerol + Deoxycholate | −3.2 C. |
| Normal Saline + 5% Dextrose + 5% Glycerol + Cholate | −2.9 C. |
| 5% Polyethylene glycol + Lactated Ringer's + 5% Dextrose | −0.8 C. |
| 5% Polysorbate (Tween) 20 + Lactated Ringer's + 5% Dextrose | −0.6 C. |
| 6% hetastarch in Lactated Ringers | −0.8 C. |
| Normal Saline + 5-10% Glycerol | −4.0 C. |
| Lactated Ringer's + 5-10% Glycerol | −3.2 C. |
| Normal Saline | −0.2 C. |
| Ice/Water | 0.4 C. |
| 20% Dextrose in Water | −1.9 C. |

The solution comprising the slurry can include agents to reduce inflammation, including but not limited to, corticosteroids, glucocorticoids, lipoxygenase inhibitors, and NSAIDs.

The solution comprising the slurry can include anesthetic agents to further reduce pain, including but not limited to, polidocanol, lidocaine, bupivacaine, prilocaine, tetracaine, procaine, mepivicaine and etidocaine.

In one embodiment, the anesthetic is QX-314, N-ethyl bromide, a quaternary lidocaine derivative that is a permanently charged molecule capable of providing long term (over 24 hours) anesthesia. Unlike lidocaine, QX-314 can provide more selective blocking of nociceptors and with longer duration of action and less side effects. QX-314 is a charged molecule that needs to enter the cell and block the sodium channels intracellularly. The ability of QX-314 to block from the inside but not the outside of neuronal membranes could be exploited to block only desired neurons. Combining QX-314 with the cold slurry injections described herein can selectively target cold sensing nociceptive sensory neurons to provide selective and long lasting anesthesia.

In another specific embodiment the slurry can be composed of a lipid emulsion, such as, e.g., Intralipid, which is an emulsion of soy bean oil, egg phospholipids and glycerin, and is available in 10%, 20% and 30% concentrations. Lipid emulsions can be mixed with amino acids and dextrose as part of a total nutrient admixture.

In another specific embodiment the slurry can be composed of a peritoneal dialysis solution.

The solution comprising the slurry can include cooled particles such as, e.g., ice particles in sizes smaller than the inner diameter of medical cannulas, catheters, and needles, e.g., smaller than about 1 mm and preferably smaller than about 0.1 mm. The volume percent, size and/or shape of cooled particles (preferably less than about 0.5 mm and nominally spherical or ovoid) can be adjusted to optimize flow of the slurry through needles catheters or cannulas and flow through the various target tissues during infusion. See, for example, Kauffeld, M et al. Int J Refrig. 2010. 33(8): 1491-1505. The volume percentage of cooled particle (e.g., ice particle) within the infused slurry and the volume of infused slurry determine cooling capacity of the infusion. In specific embodiments, the volume percentage of ice within the infused slurry can range from about 0.1% to about 50% of the solution.

II. Methods of Treatment

In a given volume of target tissue into which a slurry is infused, there are three stages of heat exchange. Initially, the slurry is much colder than the tissue as it infuses into and/or through the tissue. There is a strong thermal gradient between the tissue and the slurry that rapidly equilibrates until a local equilibrium temperature is achieved. During this rapid equilibration stage, the slurry ice melts. The amount of melting that occurs depends on the initial ice content, the local volume fraction of slurry that is mixed with tissue, the starting tissue temperature, tissue lipid content, and other factors including the slurry infusion volume and rate. These factors can be modeled using classical and numerical fluid and heat transfer approximations, e.g., with finite element models (See Example 1). If ice remains after this initial equilibration period, the equilibration temperature will be very close to the melting point of ice in the slurry, i.e., it can be from about −20° C. to about 4° C. The composition of the slurry fluid component sets the low temperature limit for this equilibration temperature, i.e., the equilibration temperature cannot be lower than depressed melting point of ice in the slurry.

After reaching a local equilibrium, the second stage begins in which ice continues to melt as heat is removed from surrounding tissues. This second stage can last for seconds to many minutes, depending on many factors. These factors include the amount of ice per unit volume that remains after the initial equilibration, dimensions of the tissue volume that contains ice, heat transfer and composition of the target and surrounding tissues, and local blood flow. The second stage can be viewed as providing a "treatment temperature and treatment time" for a target tissue, because temperature remains relatively stable in the target tissue during this time, until all of the slurry ice has melted. Treatment temperature is set mainly by composition of the slurry liquid, and volume fraction of slurry that is infused into and around the target tissue. Treatment time is set mainly by ice content and infusion variables including volume, rate and distribution, and by the size and shape of the target tissue, and by blood flow in the target tissue. For example, a greater content of slurry ice will extend the second stage; a greater infused slurry volume fraction (ratio of local infused slurry to target tissue and infused slurry) will extend this second stage; a large dimension of the infused slurry-and-target tissue will extend this stage approximately in proportion to the square of the dimension; and blood flow in the target tissue will reduce the treatment time by causing faster melting of the slurry ice. Heat transfer from the surrounding (non-slurry-filled) tissue and by blood flow, melts the slurry ice during this second stage.

In specific embodiments, the biocompatible ice slurry has a first equilibration temperature of between about 4° C. to about −30° C. and/or a second equilibration temperature of between about 2° C. to about −30° C. These equilibria temperature be achieved, for example, as follows: Using a slurry composition of hetastarch in lactated electrolyte (500 ml), saline (500 ml) and glycerol (100 ml), a slurry temperature of −5° C. can be obtained. A single bolus injection of about 25 ml of the slurry composition into tissue with a starting temperature of 29° C. can rapidly bring the tissue temperature down to −3.2° C. and maintain it below 0° C. for about 10-15 minutes; Using a slurry composition of hetastarch in lactated electrolyte (500 ml), saline (500 ml) and glycerol (50 ml), a slurry temperature of −2.1° C. can be obtained. A first bolus injection of about 50 ml into tissue using a 15 gauge needle achieves a tissue temperature of about −2° C. to −1.3° C. The temperature can be maintained below 0° C. in the tissue for about 15 minutes. When the temperature of the tissue is about −0.1° C., a second bolus injection of another 40-60 ml of slurry brings the tissue temperature down to about −1.1° C. and maintains that temperature for greater than 15 minutes. Upon a third bolus injection, the tissue temperature can be maintained below 0° C. for greater than 20 minutes. About 4-5 injections of the slurry composition can maintain cold temperatures below zero for 60 minutes to achieve hypoesthesia. Peripheral nerves subject to temperatures below zero for about 60 minutes will produce hypoesthesia for several weeks (e.g., 6-8 weeks). Thus multiple cycles of slurry injections can be done to prolong the cooling effect with slurry injection.

The rate of ice melting can be monitored in a given application and anatomic situation. For example, ice is readily seen by medical ultrasound imaging that can be used to monitor the ice content, size and shape, and rate of ice melting from a target tissue. In some applications, ice content in the treatment tissue can be monitored with ultrasound during and after infusion of the slurry. During the second stage, treatment can be greatly prolonged by providing repeated or continuous infusion of the slurry. Ultrasound guidance can be used to monitor ice content and adjust the repeated or continuous infusion of slurry accordingly.

To target a desired nerve, the location of the slurry placement can be monitored with the use of ultrasound. For example, during injection of a slurry, a targeted nerve can be monitored through the use of ultrasound to ensure correct placement of the slurry. This will allow precise delivery of the slurry and targeting of the desired nerve.

Where increased treatment time is desired, methods that temporarily limit or eliminate local blood flow can be employed. For example, mechanical forces can be applied to limit blood flow, including applying simple pressure after infusion of the slurry, or if appropriate, tourniquet application before during and after infusion of the slurry. Precooling the tissue prior to slurry injection can also induce vasoconstriction. Continuous external cooling after slurry injection can be employed to prolong the duration for which the slurry is effective in the tissue.

Methods of the invention provide reversible inhibition of peripheral nerves. After administration of the slurry, inhibition can occur for up to about 5 months; for example, inhibition of peripheral nerves can be achieved for a period of minutes, days, weeks or months after a single administration of the slurry. Multiple cycles of administrations of the slurry can be provided to extend treatment as needed. The tissue can also be prechilled or precooled prior to infusion of the slurry to allow the tissue temperature to stay cooler for extended periods of time.

Figure 2:
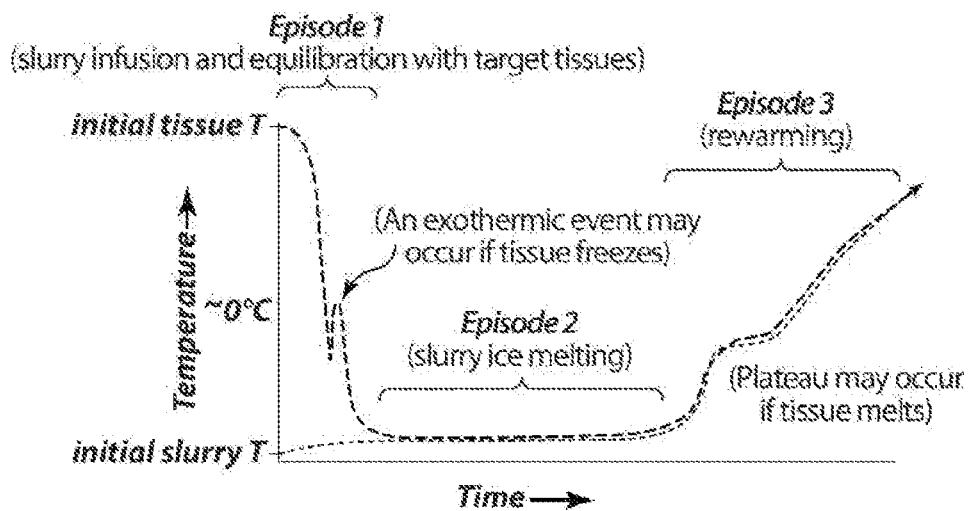
FIG. 2 depicts three stages of heat exchange following infusion of a slurry into a tissue.

The third stage after infusion of slurry occurs after the ice content has melted. The temperature of the target tissue is now able to return gradually to body temperature by the same processes that melted ice during the second stage—heat conduction, and heat convection via blood flow. It may take minutes or even hours for the target tissue to return to normal body temperature, depending again on the size, anatomy, and blood flow involved. Temperature in the target tissue increases in the third stage because all of the slurry ice has melted. These stages are illustrated schematically in FIG. 2.

Lipid-crystallization is one mechanism responsible for the temporary and prolonged loss of nerve conduction following cooling of nerves. The myelin sheath that surrounds nerve axons, contains a high concentration of lipids. A primary function of the lipid-rich sheath is to isolate the axons, such that action potentials (i.e., nerve signals) can propagate. Disruption and/or loss of the myelin sheath after local cooling appear to follow a similar mechanism, with crystallization of the myelin lipids followed by stress and degradation. The myelin sheath is a cytoplasmic extension of Schwann cells, which are slow to repair this kind of injury. Prolonged (up to approximately 3 months or more) anesthesia, pain, or itch reduction is therefore an application for this invention; for example, a slurry can be used for prolonged nerve block after injection/infusion at many of the anatomic sites that are classically used for temporary nerve blocks using an anesthetic injection.

Methods of the invention can reduce pain or itch or eliminate symptoms associated with neurological disorders such as neuropathic pain, diabetic neuropathy pain, trigeminal neuralgia, post-herpetic neuralgia, phantom limb pain, cancer related itch or pain, burn itch or pain, lichen sclerosus, scalp itch, nostalgia parasthetica, atopic dermatitis, eczema, psoriasis, lichen planus, vulvar itch, vulvodynia, lichen simplex chornicus, prurigo nodularis, itch mediated by sensory nerves, peripheral neuropathy, peripheral nerve damage, post-thoracotomy pain, incisional pain, chest pain, coccydynia, lower back pain (with or without radiculopathy), superficial scars, neuromas, acute post-operation pain, lumbar facet joint syndrome and cutaneous pain disorder.

The cutaneous pain disorder includes, but is not limited to, reflex sympathetic dystrophy (RSD), phantom limb pain, neuroma, post herpetic neuralgia, headache, occipital neuralgia, tension headaches and vulvodynia.

Methods of the invention can also be used to reduce or eliminate symptoms associated with pain disorders caused by peripheral neuropathy, peripheral nerve damage from metabolic, infectious, trauma, genetic or chemical process. Methods of the invention can also be used to reduce or eliminate cutaneous pain.

Methods of the invention can also be used to reduce or eliminate symptoms associated with pain disorders caused by surgery, such as any surgery that makes an incision through the skin and induces pain. This includes thoracic surgery pain (e.g., treatment of incisional surgical pain) caused by thoracic surgery. The slurry can be injected prior, during or after incision.

In a specific embodiment, a slurry can be used for inhibition of pain after thoracic surgery, by injection of about 3 cm$^3$ of slurry into the subcostal space. The lipid content of the exemplary subcostal nerve is about 20% ($f_{tlip}=0.2$). Prior to injection, an ice pack is applied that cools the local tissue to 20° C. ($T_t=20$). A slurry containing 30% ice ($I_o=0.3$) and with 0.001% epinephrine added for vasoconstriction, is injected around the nerve such that an approximately equal volume of slurry and tissue is created ($f_s=0.5$). After the rapid exchange based on heat capacity, temperature of the slurry-tissue mix is $T_m=(1-f_s)T_t=10°$ C. Because $T_m=10°$ C., no additional ice is melted to reach 10° C., i.e., $Q_{to10C}=(T_m-10)\rho C=0$. Latent heat is exchanged as ice in the slurry-tissue mix melts, while lipids crystallize in the myelin sheath of the target nerve. The initial ice content of the slurry-tissue mix is $I_o=f_s I_s$, which is $I_o=(0.5)(0.3)=0.15$ or 15%. With this ice content, the value of $Q_{icetotal}=f_s I_s H_{ice}$, or $(0.5)(0.3)(74)=11$ cal/cm$^3$. The lipid content of the slurry-tissue mix is $f_{mlip}=(1-f_s)f_{tlip}$, which is $(0.5)(0.2)=0.10$ or 10%. Crystallization (an exothermic process) of all the lipid in the slurry-tissue mix produces a thermal energy $Q_{tiptotal}$ equal to the lipid content times the volumetric heat of fusion for lipids, $H_{lipid}$, as given above. With its lipid content of $f_{mlip}=0.1$, and the value of $H_{lipid}=34$ cal/cm$^3$, the energy associated with lipid crystallization in the target nerve is $Q_{liptotal}=f_{mlip}H_{lipid}(0.1)(34)=3.4$ cal/cm$^3$. All of the lipid in the nerve will be crystallized because $Q_{icetotal}>Q_{liptotal}$ and residual ice remains. As this residual ice melts, the temperature drops according to the value of $Q_{iceresidual}=Q_{icetotal}-Q_{liptotal}$ which gives the value of $Q_{iceresidual}=11-3.4=7.6$ cal/cm$^3$. The final temperature is given by $T_{final}\sim10-Q_{iceresidual}/\rho C$. As mentioned, the value of $\rho C$ for most soft tissues is close to 1 cal/°C.-cm$^3$, such that $T_{final}\sim10-7.6$, or 2.4° C. Gradual warming of the =6 cm$^3$ volume of slurry-tissue mix then occurs. The diameter of a spherical volume v is given by $d=(6\ v/^-)^{1/3}$. For a 6 cm$^3$ spherical volume of slurry-tissue mix, the diameter is therefore about 22 mm. The cold slurry-tissue mix gradually warms over a time of about $(22)^2=480$ seconds, or about 8 minutes. A second or further injection of slurry can also be performed; the effectiveness of multiple cold cycles is typically greater than one cycle.

Methods of the invention can also be used to reduce muscle spasms caused by aberrant nerve firing such as bladder or facial spasms.

Methods of the invention can also be used to target motor nerves if prolonged paralysis of a motor nerve is desired.

Methods of the invention can also be used to reduce, eliminate or alter functions controlled by the autonomic nervous system. For example, the sympathetic nerve system controls hyperhidrosis through the sympathetic fibers that innervate the eccrine glands in the axilla. Methods of the invention can be used to target those autonomic nerve fibers to reduce hyperhidrosis.

The solution comprising the slurry can be administered to the peripheral nerves of the subject by injection, infusion or tumescent pumping of the slurry into a nerve or nerves such as peripheral, subcutaneous or autonomic nerves of the subject by injection into a nerve or nerves selected from the group consisting of the cutaneous nerve, trigeminal nerve, ilioinguinal nerve, intercostal nerve, interscalene nerve, supraclavicular nerve, infraclavicular nerve, axillary nerve, pudental nerve, paravertebral nerve, transverse abdominis nerve, lumbar plexus nerve, femoral nerve and sciatic nerve.

Methods of the invention can also reduce or eliminate pain associated with a nerve plexus (i.e., a group of intersecting nerves) including but not limited to the cervical plexus that serves the head, neck and shoulders; the brachial plexus that serves the chest, shoulders, arms and hands; the lumbar plexus that serves the back, abdomen, groin, thighs, knees, and calves; the sacral plexus that serves the pelvis, buttocks, genitals, thighs, calves, and feet; the celiac plexus (solar plexus) that serves internal organs; the coccygeal plexus that serves a small region over the coccyx; the Auerbach's plexus that serves the gastrointestinal tract; and Meissner's plexus (submucosal plexus) that serves the gastrointestinal tract.

Methods of the invention can also be used for renal sympathetic denervation, which is an emerging therapy for the treatment of severe and/or resistant hypertension.

Flowing the slurry through tissue allows cooling over a great distance from the infusion point, in particular through tissue structures with minimal resistance to fluid flow, e.g., along the perineural sheath of sensory or motor nerves. The solution can also be administered to any peripheral or cutaneous nerve that is accessible via a syringe needle percutaneously or through catheter via the circulatory system.

Figure 17:
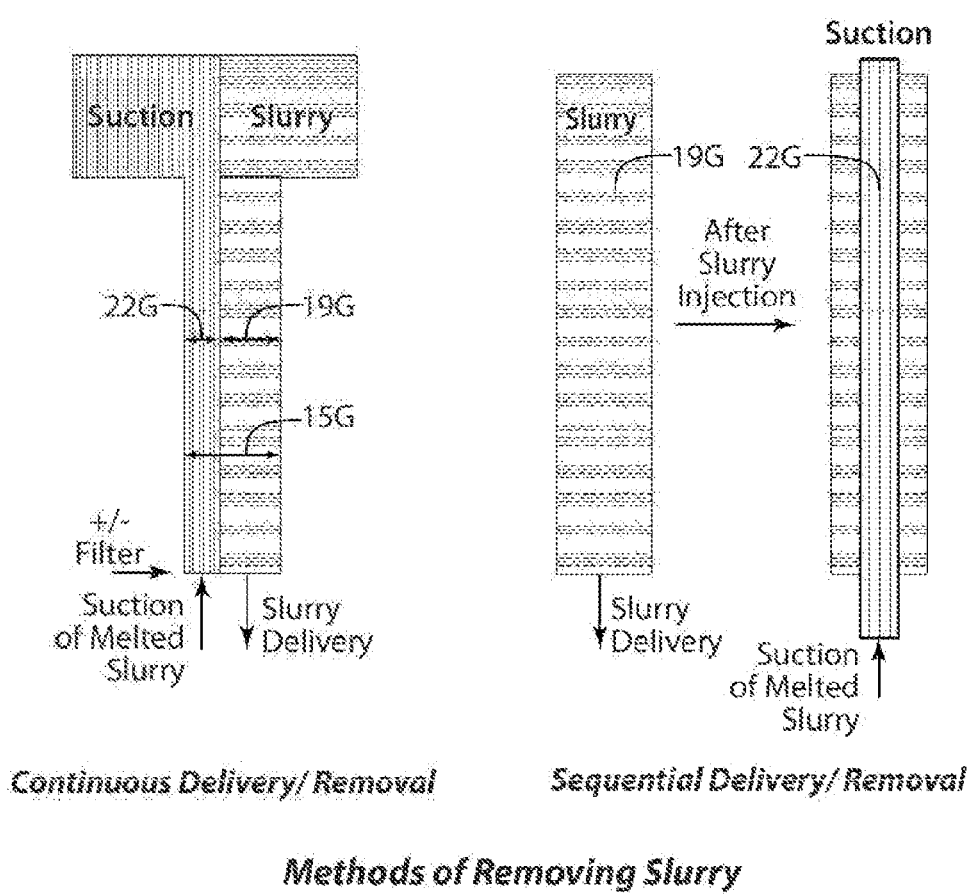
FIG. 17 depicts methods of removing slurry.

The means for injecting the slurry (for example, the needle) can include additional features, such as, e.g., a sensor for providing temperature readings to allow monitoring of target tissue temperature. The means for injecting the slurry can optionally have the ability to retrieve the melted components of the slurry, while allowing the injection of new slurry, as depicted in FIG. 17.

The location of the injection can be verified, e.g., through MRI or x-ray imaging for example, when the slurry contains imaging agents known in the art. Pre-activation of nerves and/or verification of needle placement by electric or chemical stimulation can also performed in connection with methods of the invention. Here, correct placement of the slurry can be facilitated by injecting anesthetic or electrical stimulation to produce sensation or anesthesia along the targeted nerve prior to injection of the slurry.

The duration for which a slurry is administered can be determined by a physician or other qualified professional or technician and adjusted, as necessary, to suit observed effects of the treatment or as is needed, depending on the formulation of the slurry administered. It is well within the skill in the art to adjust the duration of treatment according to the methods described herein.

Methods of the invention can also be used to treat urinary incontinence. In a recent survey among women aged 25-84 in the United States an estimated 15% report experiencing stress incontinence and 13% report experiencing urge incontinence/"overactive bladder." These two etiologies of incontinence are due to separate mechanisms, though both mechanisms may be experienced by a single patient.

Stress Incontinence is the most common type of incontinence in younger women, often from urethral hypermobility due to insufficient support of the bladder from the pelvic floor. This lack of support is due to a loss of connective tissue. This loss of support is also associated with other conditions such as pelvic organ prolapse and problems with defecation (both constipation and incontinence). At present the main treatment strategies include pharmacologic therapies, pessaries and surgical intervention, for which there are varying degrees of success. Parasympathetic, sympathetic and somatic nerves play an important function in controlling the lower urinary tract function. More specifically, the smooth muscles of the bladder—the detrusor—are innervated primarily by parasympathetic nerves; those of the bladder neck and urethra—the internal sphincter—are innervated by sympathetic nerves. The striated muscles of the external urethral sphincter (EUS) receive their primary innervation from somatic nerves. The slurries described herein could be used as an injectable therapy to treat Stress Incontinence through targeting one or more of these nerves.

Urgency incontinence is due to overactivity of the detrusor muscle. Therapies to treat urgency incontinence are primarily pharmacologic (e.g., Botulinum toxin) and are targeted toward decreasing neural input to the bladder muscle to prevent the frequent bladder spasms. Given the capacity of the ice slurries described herein to reduce nerve function, another embodiment of the invention provides treatment of urgency incontinence by inhibiting neural input to the bladder. In one embodiment, the treatment comprises an injectable therapy whereby the ice slurry is administered to, e.g., the neuromuscular junction, to inhibit neural input to the bladder.

The present invention is additionally described by way of the following illustrative, non-limiting Examples that provide a better understanding of the present invention and of its many advantages.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following Examples do not in any way limit the invention.

Example 1: Quantitative Model to Illustrate the Behavior of Injected Slurries Simplifying and reasonable assumptions are made in a quantitative model to illustrate the behavior of injected slurries, as depicted in FIG. 1.

Heat capacity is an important component of the heat exchange between a slurry and a tissue. The first heat exchange to consider is that of the energy stored by the heat capacity of slurry and tissue. The energy per unit volume in a medium stored by heat capacity is given by $H=T\rho C$, where H is energy density (cal/cm³), T is temperature (° C.), $\rho$ is density (gm/cm³) and C is specific heat capacity (cal/C. gm). Assume that $\rho C$ is the same for slurry and tissue and water, i.e. $\rho C=1$ cal/gm-° C. This assumption is approximately true for all soft tissues except fat, for which $\rho C$ is lower by about a factor of 2.

Consider a local volume of tissue into which slurry has been introduced. When slurry is introduced with a volume fraction of $f_s$ into local tissue, the local tissue occupies a volume fraction of $(1-f_s)$. The stored heat per unit volume of the resulting slurry-tissue mix due to heat capacity of the slurry is $H_s=f_s T_s \rho C$, and the stored heat per unit volume due to heat capacity of the tissue is $H_t=(1-f_s)T_t\rho C$. After rapid exchange of the thermal energy due to heat capacity, a new temperature $T_m$ is achieved. Thermal energy due to heat capacity of the mix is given by $H_m=T_m\rho C$. Conservation of energy in the local heat exchange requires that $H_s+H_t=H_m$. Combining equations:

$$f_s T_s \rho C + (1-f_s)T_t \rho C = T_m \rho C$$

Solving for $T_m$, the slurry-tissue mix temperature after this initial part of heat exchange:

$$T_m = f_s T_s + (1-f_s)T_t$$

Because the temperature of physiological ice slurries is generally close to 0, this simplifies to:

$$T_m = (1-f_s)T_t$$

The rapid heat exchange upon mixing due to heat capacity alone is the volume-weighted average of the two starting temperatures. For example, if $f_s=0$, no slurry is added, and $T_m=T_t$, the starting tissue temperature. If $f_s=1$, the mix is all slurry, and $T_m=0$. If $f_s=0.5$, there is a 50-50 mix of slurry and tissue, and the resultant temperature after mixing is the average of the slurry and the tissue starting temperatures. Typical values of $f_s$ for interstitial injection of a slurry range from about 0.2 to about 0.8, i.e., the mixed slurry-tissue volume may have about 20% to 80% slurry content. Also consider the situation of $f_s=0.5$. If the starting tissue temperature $T_t$ is 37° C., then $T_m=18.5°$ C. after exchange of heat from heat capacity.

The volume fraction of ice in a physiological slurry in this model is defined as $I_s$, being the volume of ice per unit volume of slurry. Immediately after injection into tissue, the initial volume fraction of ice in the local slurry-tissue mix, is therefore:

$$I_o = f_s I_s$$

$I_o$ is the total amount of ice available for melting, per unit volume of the slurry-tissue mix.

After the rapid heat exchange from heat capacity, ice in the slurry component of the slurry-tissue mix begins to melt, absorbing heat and cooling the slurry-tissue mix. Ice in the slurry-tissue mix melts until it is gone, or until an equilibrium temperature is reached, before the period of gradual warming by body heat exchange briefly discussed above. In pure water, ice and liquid water can co-exist at equilibrium temperatures between 0° C. and 4° C. In tissue, there are numerous solutes that cause freezing point depression, such that ice and water co-exist over a somewhat lower temperature range, e.g., about –8° C. to 0° C. in skin. Lipids in the tissue are in a liquid state at normal body temperature. As cooling of the slurry-tissue mix occurs due to ice melting, below a certain temperature lipids can crystallize. In essence, there is a heat exchange between the latent heat of fusion from melting ice, and the latent heat of fusion from lipid crystallization. These two processes proceed in opposite directions (e.g., the water melts, the lipids crystallize) because lipid crystallization occurs at temperatures considerably higher than the freezing point of water. Most animal fats crystallize at between 10° C. and 15° C., depending on the length and saturation of the lipid chains in triglyceride molecules. Wax esters and free fatty acids crystallize at similar temperatures. Polar lipids crystallize at lower temperatures, for example the phospholipids of cell membranes can remain somewhat fluid even well below 0° C.

Injected physiological slurries are effective to inhibit pain or itch by affecting nerve myelin sheath lipids. Lipids of the sheath crystallize well above 0° C. Effective treatment depends on variables including the starting tissue temperature $T_t$, the ice content of slurry $I_s$, the amount and speed of slurry injected to achieve an adequate slurry fraction $f_s$ in the slurry-tissue mix, the target lipid content of the tissue $L_t$, its crystallization temperature $T_c$, and the time for which some ice remains in the slurry-tissue mix.

Enthalpy of fusion (also called heat of fusion), describes how much thermal energy is absorbed (endothermic) or released (exothermic) due to changing from solid to liquid state. The melting of ice is an endothermic transition requiring a large amount of thermal energy. For water, the heat of fusion is 80 cal/gm. The density of ice at 0° C. is 0.92, such that the volumetric heat of fusion, $H_{ice}$ (the heat energy needed to melt a volume of ice) is:

$$H_{ice} = 74 \text{ cal/cm}^3$$

The total heat per unit volume that can be absorbed by melting all of the ice in the slurry-tissue mix, $Q_{icetotal}$, is simply its total ice content multiplied by $H_{ice}$:

$$Q_{icetotal} = f_s I_s H_{ice}$$

Typical values as mentioned above for $f_s$ range from about 0.2 to 0.8, and the ice content of physiological slurry can be up to about 50% ($I_s \sim 0.5$). For the approximate maximum of $I_s=0.5$, the range (without limitation) for $Q_{icetotal}$ in the slurry-tissue mix is therefore about 7 to 30 cal/cm³.

The heat of fusion for animal fat lipids ranges from about 30-50 cal/gm (*Cooling Technology in the Food Industry*; Taylor and Francis, 1976). The density of lipids range from about 0.8-0.9 gm/cm³ (e.g., palmitic triglyceride in solid phase is 0.85 gm/cm³). Taking the mean value of 40 cal/gm as the heat of fusion, the latent heat per unit volume for crystallization of lipids is about:

$$H_{lipid}=34 \text{ cal/cm}^3.$$

Thus, the latent heat for crystallization of lipids is less than half of that for melting of ice. Cooling of the slurry-tissue mix proceeds by some ice melting, until the temperature reaches about 10° C., the temperature necessary for lipid crystallization to begin. The thermal energy from consumed by dropping the temperature of the slurry-tissue mix to about 10° C. is given by:

$$Q_{to10C}=(T_m-10)\rho C.$$

At about that temperature, whatever ice remains from the slurry will melt, absorbing the energy necessary to crystallize about twice its own volume of lipid. If all of the tissue lipid is crystallized, more ice will melt and the temperature will drop below about 10° C., potentially into the approximately −8° C. to 0° C. range at which ice and liquid water can coexist in tissue. The lipid content of the slurry-tissue mix is therefore another important factor. Defining the lipid content of the tissue as $f_{tlip}$, the lipid content of the slurry-tissue mix is:

$$f_{mlip}=(1-f_s)f_{tlip}.$$

The value of $f_{tlip}$ depends on tissue type. The lipid content of most soft tissues ranges from about 5% (most connective tissues) to about 80% (fat), i.e., $f_{tlip}$=0.05 to 0.8. The energy per unit volume of the slurry-tissue mix that is produced by crystallizating all of the lipid present, is:

$$Q_{liptotal}=f_{mlip}H_{lipid}$$

During the period of latent heat exchange between ice melting and lipid crystallization in the slurry-tissue mix, ice in the slurry melts until all of the lipid is crystallized, or until the ice is gone.

The fraction of the lipid in the slurry-tissue mix that crystallizes is simply given by the energy balance:

$$f_{lipxtal}=(Q_{icetotal}-Q_{to10C})/Q_{liptotal}$$

If $(Q_{icetotal}-Q_{to10C})<Q_{liptotal}$ a fraction of the lipid will crystallize, given above by $f_{lipxtal}$. If $(Q_{icetotal}-Q_{to10C})=Q_{liptotal}$, all of the lipid will crystallize and all of the ice will melt; the temperature will remain near about 10° C., the phase transition temperature for most animal lipids. If $(Q_{icetotal}-Q_{to10C})>Q_{liptotal}$, all of the lipid will crystallize, and the temperature will thereafter decrease below about 10° C. until all of the ice is melted or until an equilibrium exists between ice and liquid water in the tissue, i.e., in the temperature range of about −8° C. to 0° C. The lowest temperature reached is determined by heat exchange between the residual ice melting, and the heat capacity of the slurry-tissue mix. The lowest temperature $T_{final}$ can therefore be estimated by equating the latent heat per unit volume absorbed by melting of the residual ice, with the heat associated with heat capacity of the temperature drop below about 10° C.

The latent heat associated with the residual ice melting after the lipid is crystallized is $Q_{iceresidual}=Q_{icetotal}-Q_{to10C}-Q_{liptotal}$, and the amount of residual ice per unit volume is $I_{residual}=Q_{iceresidual}/H_{ice}$. The temperature drop to $T_{final}$ due to residual ice melting can be estimated by:

$$Q_{iceresidual}=(10-T_{final})\rho C, \text{which rearranges to}$$
$$T_{final}=10-Q_{iceresidual}/\rho C$$

The local heat exchanges modeled above occur over a time scale of seconds because the slurry is intimately in contact with tissue, by mixing flowing and/or dissecting through the soft tissue during interstitial injection. After exchange of the latent heats from melting ice and crystallizing lipids, the temperature of the slurry-tissue mix settles at about $T_{final}$, then gradually warms due to conduction and convection. The rate of gradual warming depends therefore on the rates of conduction and convection. In the absence of blood flow (convection), warming by conduction involves a minimum characteristic time, proportional to the square of the diameter of the local slurry-tissue mix. Typically in soft tissues, the time in seconds for substantial warming of a region by conduction (to 1/e of a final equilibrium value) is approximately equal to the square of the diameter in millimeters. For example, a 10 mm diameter slurry-tissue mix would typically takes about 100 seconds for substantial warming, and a 30 mm diameter slurry-tissue mix would typically takes about 900 seconds (i.e., 15 minutes) for substantial warming by conduction. Depending on the ice content, some ice may remain even after this estimated period of substantial warming. The model presented here is illustrative, not exact. Direct measurement of slurry and tissue temperatures can be performed. As shown below, such measurements are generally consistent with this approximate model.

Example 2: Inhibition of Sciatic Nerve Function in Rats

Figure 3:
FIG. 3 depicts a rat sciatic nerve, exposed via surgical dissection.
Figure 4:
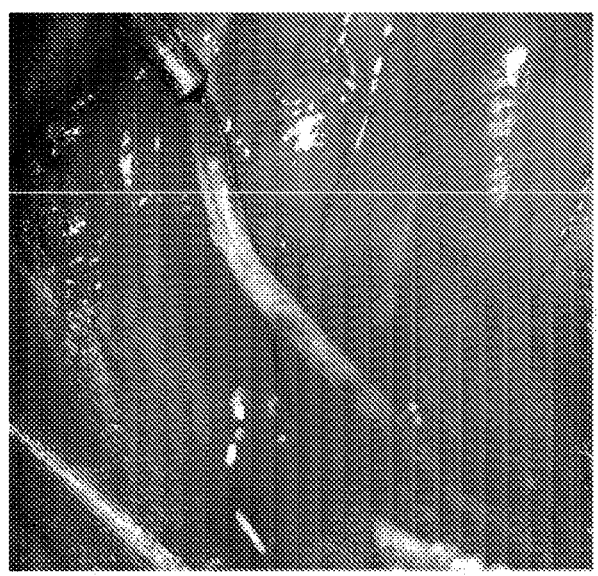
FIG. 4 depicts a thermocouple placed under a rat sciatic nerve to record tissue temperature.

A 6% hetastarch lactated Ringer's slurry (i.e., hetastach (500 ml), saline (500 ml) and glycerol (50 ml), blended together) was injected on top of the sciatic nerve of a male rat weighing about 250-271 g. The procedure was conducted as follows: The rat was placed under general anesthesia using inhaled isoflurane and oxygen. The sciatic nerve was exposed via surgical dissection (FIG. 3). A starting slurry temperature of −3.2° C. to −2.7° C. was obtained and maintained throughout the experiment. For each of five injections, 5 ml of slurry was injected on top of the sciatic nerve. A thermocouple placed under the sciatic nerve was used to record tissue temperature (FIG. 4).

Figure 5:
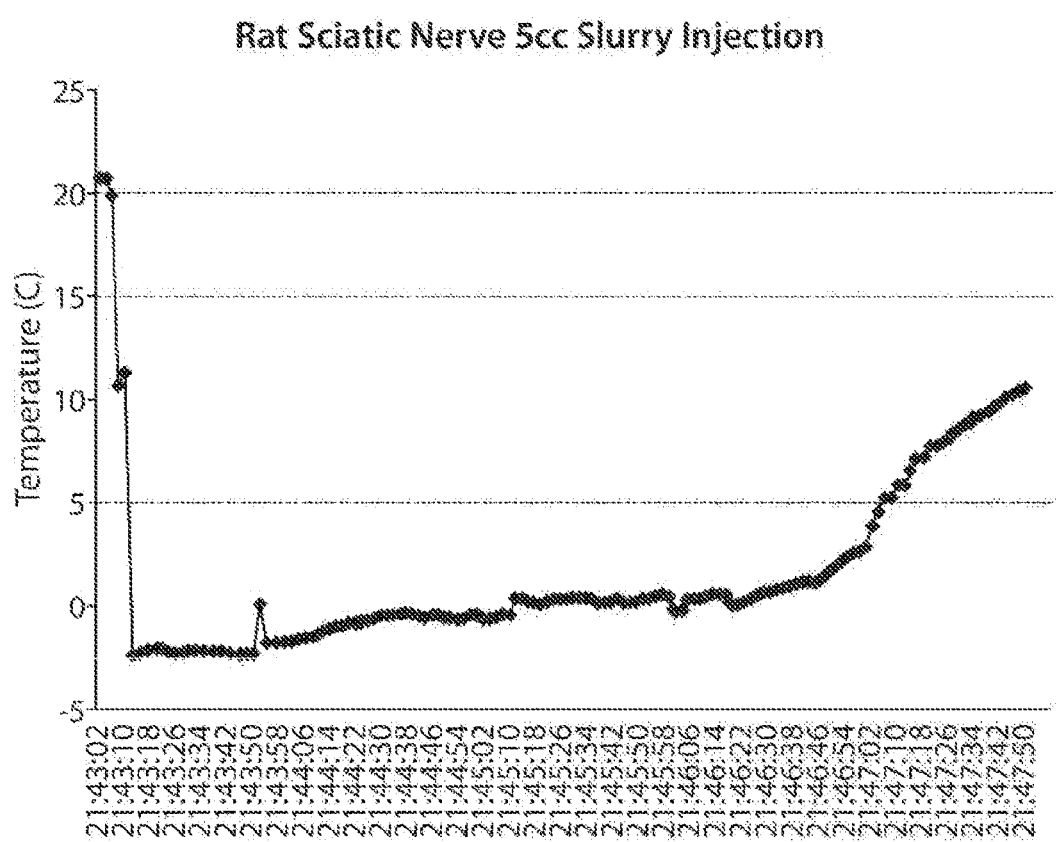
FIG. 5 depicts tissue temperature following injection of a 6% hetastarch lactated ringer slurry on top of a live rat sciatic nerve.
Figure 6:
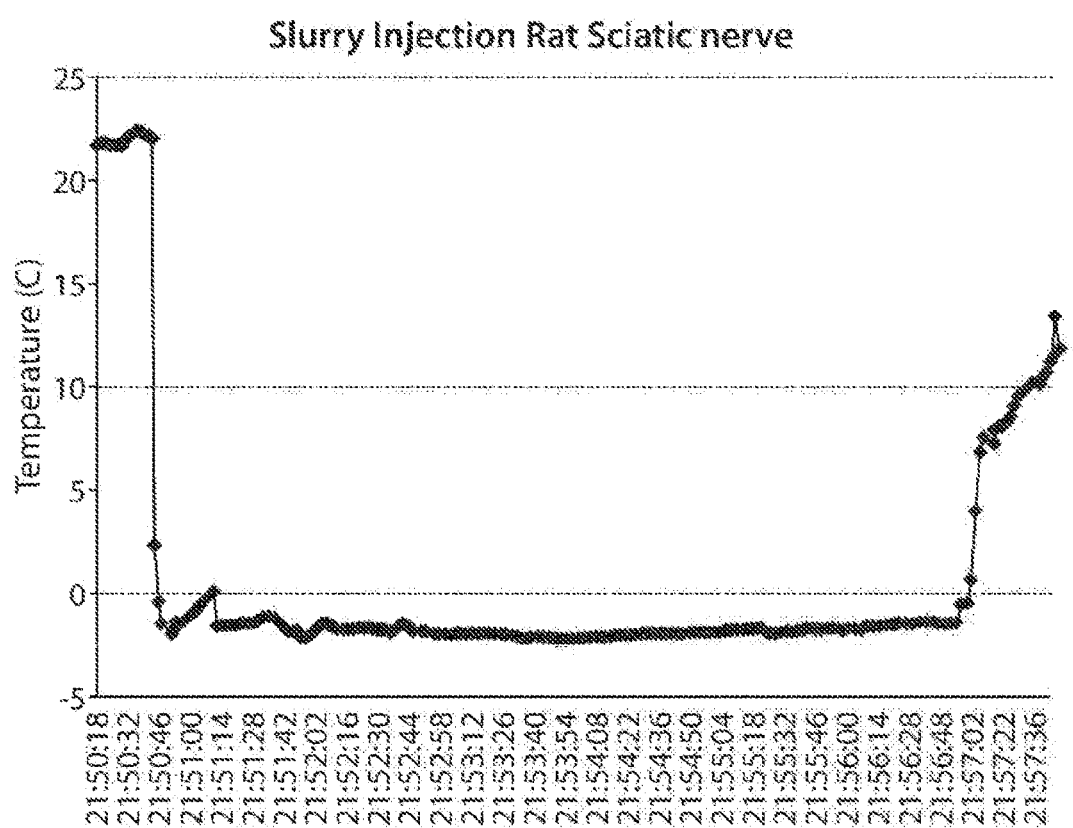
FIG. 6 depicts tissue temperature following injection of a 6% hetastarch lactated ringer slurry on top of a live rat sciatic nerve.
Figure 7:
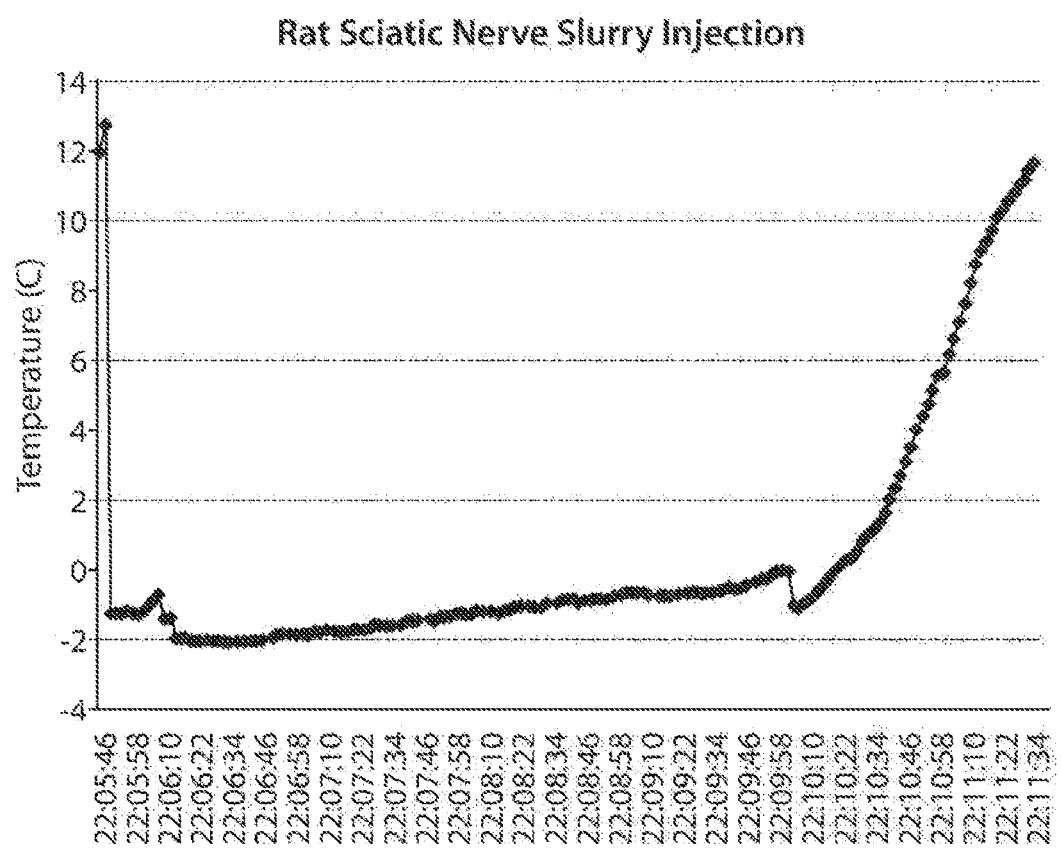
FIG. 7 depicts tissue temperature following injection of a 6% hetastarch lactated ringer slurry on top of a live rat sciatic nerve.

The 6% hetastarch lactated Ringer's slurry can maintain nerve tissue temperature below 0° C. for an average of 5 minutes and the tissue temperature was maintained as long as ice was present in the slurry (FIGS. 5, 6 and 7). The nerve block is predicted to last days, weeks or months. When the ice turned to liquid, the tissue temperature rapidly rose above zero. Precooling the tissue around the nerve made the slurry last longer, as melting of the ice occurred at a slower rate (FIG. 6).

Example 3: Rat Sensory Testing

The efficacy of cold therapy in large motor and sensory nerve, such as the sciatic nerve, can be demonstrated in a rodent model by assessing nerve tissue staining and conducting assays to measure motor and sensory function following injection of cold slurry. Sensory experiments were conducted on 12 adult male rats having a mass between 250 grams and 350 grams. The rats were habituated to the testing environment, labeled 1-12, and randomized into 2 groups of 6 rats each. Baseline sensory testing was performed 1 day prior to the procedure.

Figure 8:
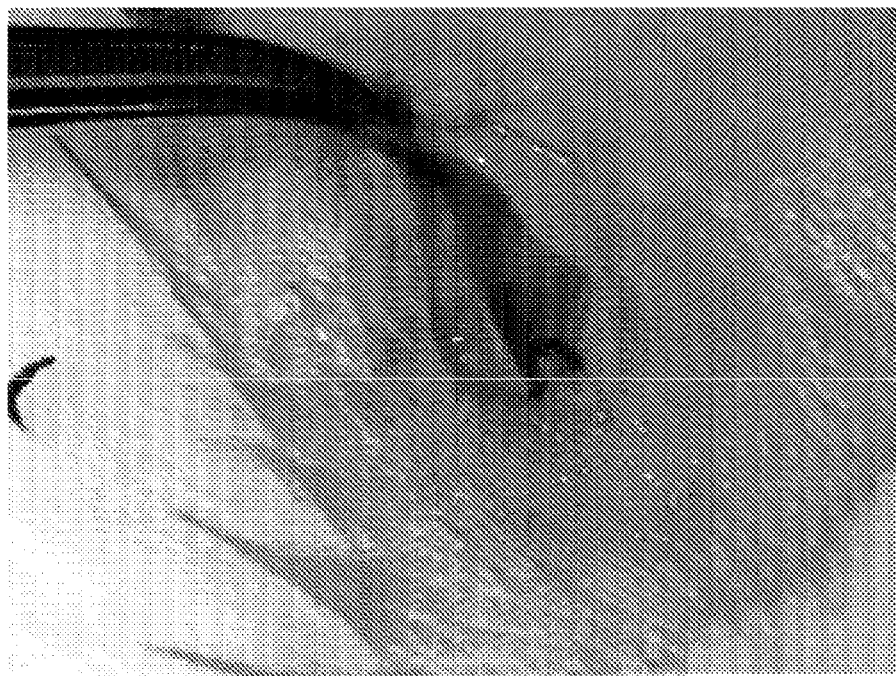
FIG. 8 depicts the blunt exposure of the common sciatic nerve through the biceps femoris and separation from adjacent tissue.

All rats received chronic constriction injury (CCI) to model chronic neuropathic pain. The common sciatic nerve was exposed using blunt dissection through the biceps femoris and was separated from adjacent tissue as depicted in FIG. 8. A 4-0 chromic gut suture was loosely tied around the nerve at 2 points about 1 mm apart from each other. The desired degree of constriction retards, but does not arrest, circulation through the superficial epineurial vasculature.

Figure 9:
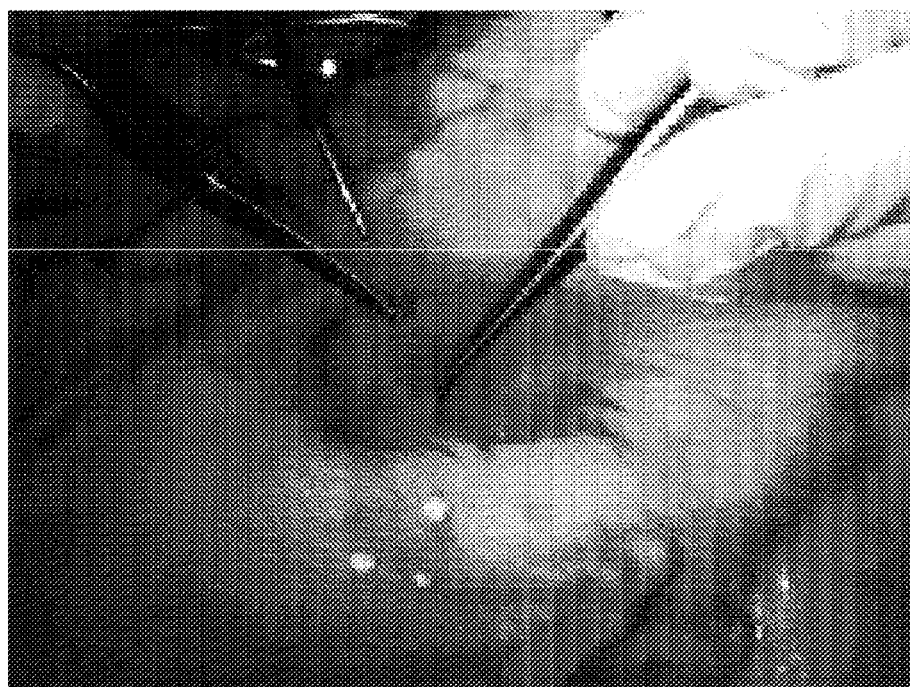
FIG. 9 depicts the injection of ice slurry.

Sensory testing was repeated on the rats 6 days post-CCI to demonstrate efficacy of the procedure, i.e., the rats were more sensitive to heat injury on the injured paw than the uninjured paw and withdrew their injured paw much more quickly when exposed to heat pain. All rats had the sciatic nerve exposed using blunt dissection 1 week post-CCL Six rats received an injection of ice slurry as depicted in FIG. 9. Six rats were opened and closed without slurry injection (nonslurry).

The slurry injected into the six rats in the experimental group consisted of 5% glycerol (by weight) in normal saline, plus a 5% glycerol spike (by weight) prior to injection. 10 cc of slurry was injected around the sciatic nerve in each rat. A thermocouple was placed beside the nerve to record the temperature. The mean temperature of the slurry overlying the sciatic nerve at the time of injection was about −1.1° C. When the temperature reached +5° C., the area was blotted with sterile gauze and an additional 10 cc of slurry was injected around the sciatic nerve again. The tissue temperature in the injection site reached +5° C. in about 5 minutes on average.

All rats tolerated injection of slurry well. There was no evidence of necrosis, infection, ulceration, or self-mutilating behaviors.

Sensory testing was performed to test the potential analgesic effect of the ice slurry at days 14, 20, 25, 32, 36, and 42 post-slurry-injection. Although all rats were randomized, some rats responded better to the chronic constriction injury by becoming more hypersensitive to thermal pain as expected. These rats were used to assess reduction of thermal pain by injection of ice slurry. The results are shown in the Figures described below.

Figure 10:
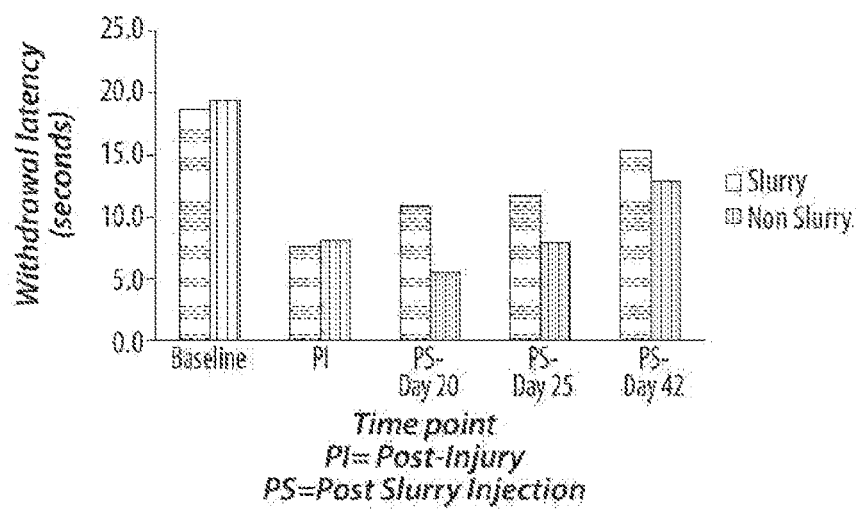
FIG. 10 depicts the thermal paw withdrawal latencies of rats with chronic constriction sciatic nerve injury. Following the constriction sciatic nerve injury, responder rats were either treated with slurry or left untreated (nonslurry). Increase in thermal withdrawal latency response times to a heat exposure in rats exposed to the slurry at 20, 25, and 42 days post-slurry was observed indicating decreased pain to thermal stimuli.

FIG. 10 depicts the thermal hindpaw withdrawal latencies of responder rats showing longer response times to a heat exposure in rats at 20, 25, and 42 days post-slurry-injection. Longer response times indicate less pain from thermal stimuli indicating that slurry reduces thermal pain.

Figure 11:
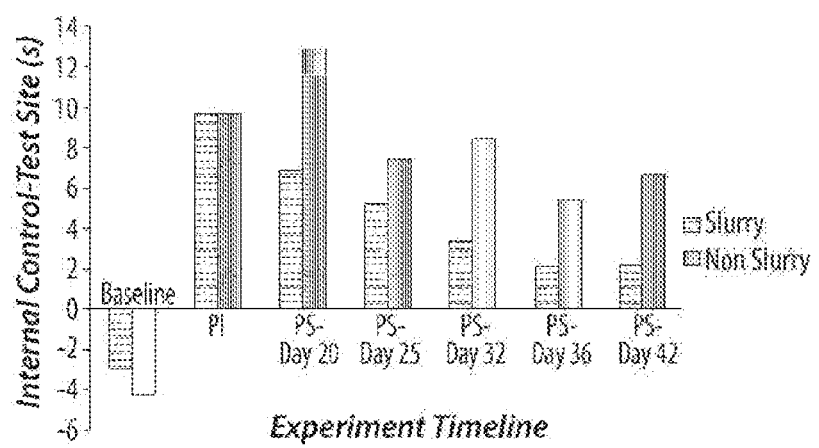
FIG. 11 depicts testing results by comparing differences in thermal withdrawal latencies of responder rates with normalization to internal control.

Because sensory testing in rats is known to be variable one method of reducing the variability is reporting the difference between the test side (left hindpaw) and the internal control (right hindpaw), i.e., right hindpaw latency minus left hindpaw latency. FIG. 11 depicts testing results by comparing differences in thermal withdrawal latencies of responder rats with normalization to internal control. A positive value indicates that the left paw withdraws quicker to heat pain than the right. Declining differences in latency between the left paw and the right paw can be seen after slurry injection indicating that slurry reduces thermal pain.

Experiment 4: Tolerance to Various Slurry Compositions

The slurries listed in Table 3 were generated and successfully injected around the rat sciatic nerve. "NS" is an abbreviation for "normal saline" (0.90% grams NaCl per ml $H_2O$). "hetastarch" is another term for "hydroxyethyl starch", a nonionic starch derivative. HEXTEND® (6% hetastarch lactated electrolyte injection having an average molecular weight of 670,000 Daltons and available from Hospira, Inc. of Lake Forest, Illinois) was used for the experiment conducted herein. "LR" is an abbreviation for lactated Ringer's solution Percentages of glycerol are expressed in terms of g/ml.

TABLE 3

| Exemplary Slurries |
| --- |
| NS + 5% glycerol |
| NS + 10% glycerol |
| NS + 20% glycerol |
| Hetastarch + 5% glycerol |
| LR + 10% glycerol |

One week post injection all rats were checked for tolerability side effects via observation and via dissection of the injected area and gross inspection. All the animals tolerated the injection with no sign of infection, ulceration, necrosis or side effects up to one week after the injection.

Table 4 below details additional safety and tolerability testing on rats. Tattoo ink was added to show the localization of the injected slurry around the sciatic nerve.

TABLE 4

Further Safety and Tolerability Testing

| Rat | Slurry Composition | Injection Site | Temp (° C.) | Amount Injected (cc) |
| --- | --- | --- | --- | --- |
| 1. | NS + 5% glycerol | R thigh sciatic | −2.0 | 7-10 |
| 2. | NS + 10% glycerol | R thigh sciatic | −2.2 | 7-10 |
| 3. | NS + 10% glycerol + Tattoo Ink | R thigh sciatic | −2.1 | 7-10 |
| 4. | NS + 10% glycerol + Tattoo Ink | R thigh sciatic | −2.8 | 7-10 |
| 5. | NS + 20% glycerol + Tattoo Ink | R thigh sciatic | −3.9 | 7-10 |
| 6. | NS + 20% glycerol + Tattoo Ink | R thigh sciatic | −4.0 | 7-10 |
| 7. | Hetastarch + 5% glycerol | R thigh sciatic | −4.3 | 7-10 |
| 8. | Hetastarch + 5% glycerol | R thigh sciatic | −4.3 | 7-10 |
| 9. | LR + 10% glycerol | R thigh sciatic | −3.0 | 7-10 |
| 10. | LR + 10% glycerol | R thigh sciatic | −3.1 | 7-10 |
| 11. | Ice flakes in cold hetastarch ± glycerol | R thigh sciatic | −0.2 | 7-10 |
| 12. | Ice flakes in cold hetastarch ± glycerol | R thigh sciatic | 0.0 | 7-10 |

Figure 13:
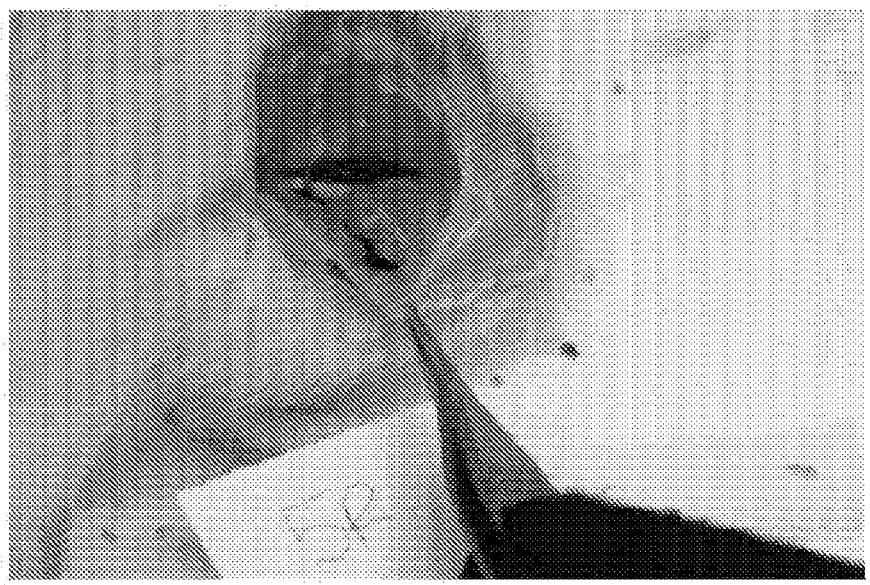
FIG. 13 verifies the blind injection of an ice slurry stained with tattoo ink for visualization adjacent to the rat sciatic nerve.

No evidence of infection, tissue necrosis or ulceration in any of the rats was seen in any of the rats at 24, 48, and 72 hours post-injection. The muscle remained intact grossly. There were no differences in necropsy observations between the side injected with slurry and the side not injected with slurry 1 week post-injection. Tattoo ink was found localized around the nerve indicating that slurry was injected precisely around the target tissue (FIG. 13).

An additional study was performed to explore the safety and tolerability limits of cryoslurries with increasing amount of glycerol injected around the sciatic nerve of rats. The rats were observed daily for one week post injection, and were checked for tolerability of side effects via observation, photography and histology. The results are shown in Table 5.

TABLE 5

Further Safety and Tolerability Testing

| Rat # | Slurry Composition | Slurry Temperature | Injection Site | Amount Injected |
|---|---|---|---|---|
| 5 | NS + 20% Glycerol | −5.2 C. | R Sciatic | 15 cc |
| 4 | NS + 30% Glycerol | −6.7 C. | R Sciatic | 10 cc |
| 3 | NS + 30% Glycerol | −7.4 C. | R Sciatic | 9-10 cc |
| 2 | NS + 40% Glycerol | −8.2 C. | R Sciatic | 9-10 cc |
| 1 | NS + 40% Glycerol | −10.1 C. | R Sciatic | 9-10 cc |

All of the animals tolerated the injection with no sign of infection, ulceration, necrosis or side effects up to one week after the injection, at which time the animals were sacrificed. No abnormalities were noted at time of necropsy.

Example 5: Relationship of Solute Concentration to Slurry Temperature

Figure 12:
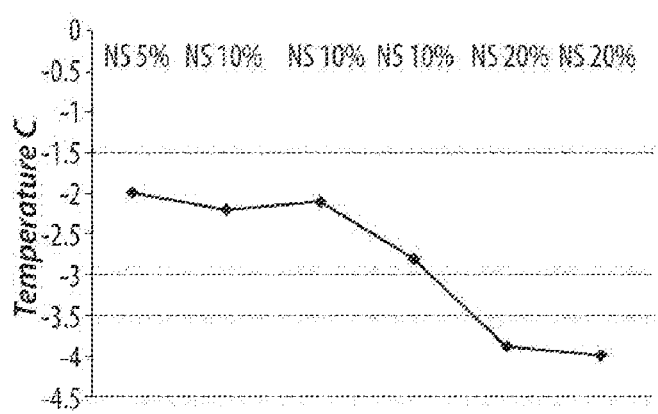
FIG. 12 depicts the effect of increasing glycerol concentrations (in normal saline) on slurry temperatures.

In FIG. 12, the effect of increasing glycerol concentrations (in normal saline) on slurry temperatures are depicted. Increasing the amount of glycerol in the slurry led to dramatic drop in slurry temperature. The safety and tolerability limit of lowest tolerable slurry temperature was tested with the injection s of slurries shown in Table 5. All of the animals tolerated the injection with no sign of infection, ulceration, necrosis or side effects up to one week after the injection, at which time the animals were sacrificed. No abnormalities were noted at time of necropsy.

Example 6: Feasibility of Blind Cryoneurolysis Injections

Referring now to FIG. 13, tattoo ink (black pigment) was added to a slurry composed of normal saline and 20% glycerol. This slurry was injected in a Sprague-Dawley rat, into the anatomic pocket containing the sciatic nerve. One week post-injection, the rat was sacrificed, and the skin overlying the anatomic pocket containing the sciatic nerve was then dissected to confirm the placement of the slurry (visible due to the tattoo ink) adjacent to the sciatic nerve. This image demonstrates the feasibility of delivering slurry around the sciatic nerve by blind injection through the skin.

Example 7: Rat Sensory Testing

Additional sensory testing was conducted on Sprague-Dawley rats that were habituated to the environment of sensory testing for three consecutive days prior to obtaining baseline measurements. Baseline sensory testing of thermal withdrawal latencies was performed. Thermal withdrawal latencies represent the amount of time it takes a rat to withdraw its hindpaw from an infrared heat source, thus a higher value means a higher threshold for pain and a lower value means that the rat has increased sensitivity to pain. All rats received chronic constriction injury (CCI) to model chronic neuropathic pain. The common sciatic nerve was exposed using blunt dissection through the biceps femoris and was separated from adjacent tissue. A 4-0 chromic gut suture was loosely tied around the nerve at 2 points about 1 mm apart from each other. The desired degree of constriction retards, but does not arrest, circulation through the superficial epineurial vasculature. Sensory testing was repeated on the rats 6 days post-CCI to demonstrate efficacy of the procedure. All rats had the sciatic nerve exposed using blunt dissection 1 week post-CCI.

The slurry injected into the rats in the experimental group consisted of 10% glycerol (by weight) in normal saline, and had a mean temperature of −3.9° C. A thermocouple was placed beside the nerve to record the temperature. Initially, 5 cc of slurry was injected onto the nerve in each rat. Subsequently, using a syringe smaller than the delivery syringe, slurry was continuously removed from the site as it melted and was replaced with new ice slurry. A 15 minute cooling duration of the nerve was ensured, defined as a temperature of less than +5° C. at the site of the nerve. A sample of the slurry was removed from the container and allowed to warm to room temperature. This room temperature solution of identical composition to the slurry was injected into control (room temperature slurry) rats.

All rats tolerated injection of the slurry well. There was no evidence of necrosis, infection, ulceration, or self-mutilating behaviors. Sensory testing was performed to test the potential analgesic effect of the ice slurry at an intermediate time point (Days 5 and 6 post slurry injection) and then a long term time point (Day 28 post slurry injection). Selected rats were able to be matched on the basis of mean injury severity post CCI. Injury severity was determined by reduction of thermal withdrawal latency compared to the mean baseline measurement: Injury Severity=(Baseline Thermal Withdrawal Time)−(Thermal Withdrawal Time at Time Point X). Hence, a reading of 0 would indicate that the rat has returned to its baseline (pre-injury) pain threshold. There were four rats that had perfect matches (≤0.2 s difference), and then an additional two rats were matched by highest level of severity in the group (≤0.5 s difference).

Figure 14:
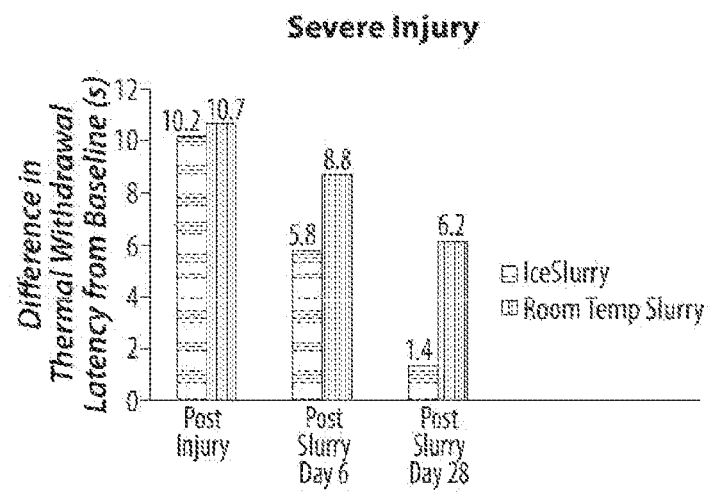
FIG. 14 depicts the thermal paw withdrawal latencies of rats with chronic constriction sciatic nerve injury scored as "severe." Differences in paw withdrawal latencies from baseline after injection of room temperature and ice slurries show that ice slurry induces decreased pain sensation after the injury.

In rats with severe sciatic constriction injury, the addition of ice slurry reduced their pain level to thermal stimuli at day 6 and day 28 post injection (FIG. 14). When compared to the rat injected with room temperature slurry (shown in red), the one injected with ice slurry (shown in blue) had a 4.4 fold reduction in thermal withdrawal latency at day 28 post ice slurry injection (1.4 s vs 6.2 s), indicating significantly reduced thermal pain sensitivity.

Figure 15:
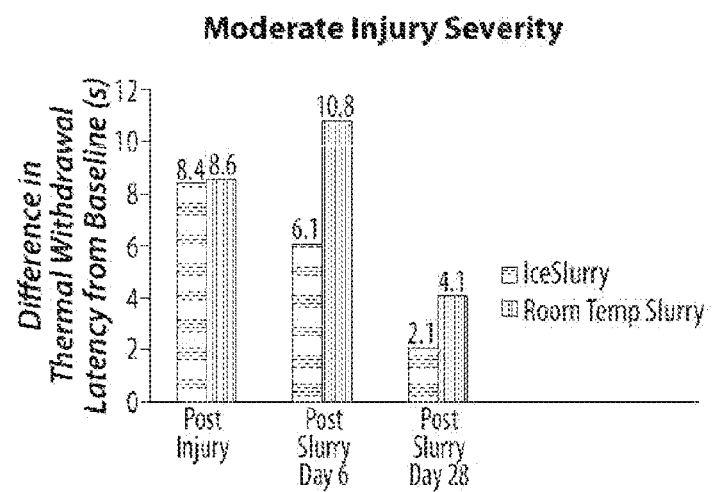
FIG. 15 depicts the thermal paw withdrawal latencies of rats with chronic constriction sciatic nerve injury scored as "moderate." Differences in paw withdrawal latencies from baseline after injection of room temperature and ice slurries show that ice slurry induces decreased pain sensation after the injury.

In rats with moderate sciatic constriction injury, the addition of ice slurry reduced their pain level to thermal stimuli at day 6 and day 28 post injection (FIG. 15). When compared to the rat injected with room temperature slurry (shown in red), the one injected with ice slurry (shown in blue) had an almost 2 fold reduction in thermal withdrawal latency at day 28 post ice slurry injection (2.1 s vs 4.1 s) indicating significantly reduced thermal pain sensitivity.

Figure 16:
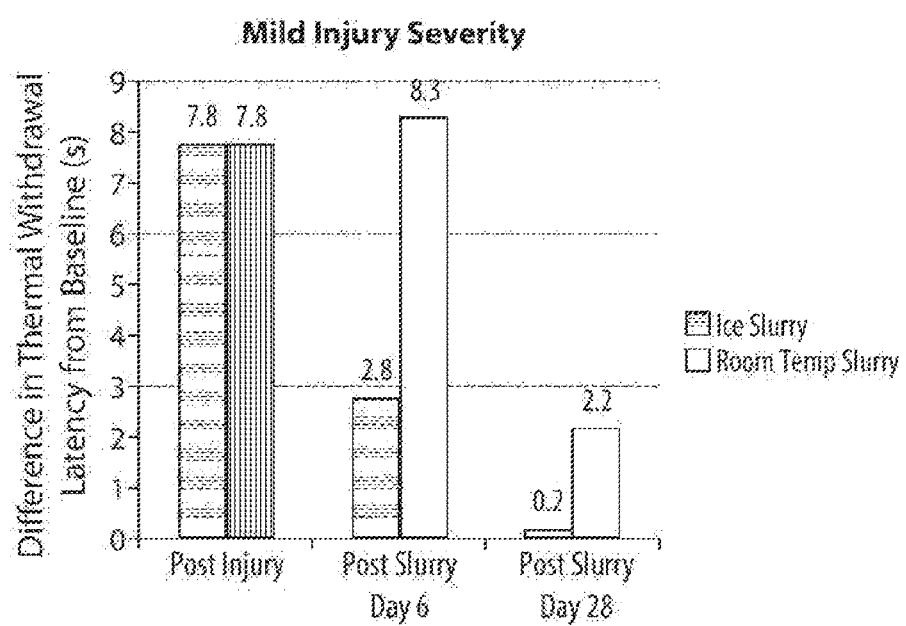
FIG. 16 depicts the thermal paw withdrawal latencies of rats with chronic constriction sciatic nerve injury scored as "mild." Differences in paw withdrawal latencies from baseline after injection of room temperature and ice slurries show that ice slurry induces decreased pain sensation after the injury.

In rats with mild sciatic constriction injury, the addition of ice slurry reduced their pain level to thermal stimuli at day 6 and day 28 post injection (FIG. 16). When compared to the rat injected with room temperature slurry (shown in red), the one injected with ice slurry (shown in blue) had an 11 fold reduction in thermal withdrawal latency at day 28 post ice slurry injection (0.2 s vs 2.2 s) indicating significantly reduced thermal pain sensitivity. In fact, by day 28 the ice slurry injected rats had thermal sensitivity equivalent to baseline levels which means that addition of ice slurry reduced the pain level back to baseline.

Example 8: Injection of Slurry Around the Sciatic Nerve of Naïve (Uninjured) Rats Male Sprague-Dawley rats weighing 250-271 g were obtained and underwent baseline sensory testing. Thermal withdrawal latencies of the hindpaws were obtained. Subsequently, the rats were anesthetized with inhaled isoflurane and oxygen, and their left thigh area was shaved and cleaned. Slurries of the following compositions shown in Table 6 were then injected into the anatomic pocket containing the left sciatic nerve:

TABLE 6

Injected Slurry Compositions

| Slurry Composition | Temperature | Amount Injected | Number of Rats Injected |
|---|---|---|---|
| Intralipid* | −1.0 C. | 10 cc | 2 |
| 2.5% Urea in Normal Saline | −2.9 C. | 10 cc | 2 |
| 6% hetastarch in Lactated Ringer's | −0.3 C. | 10 cc | 2 |
| Normal Saline + 5% Glycerol + Epinephrine + Isolecithin** | −3.0 C. | 10 cc | 2 |

Figure 18:
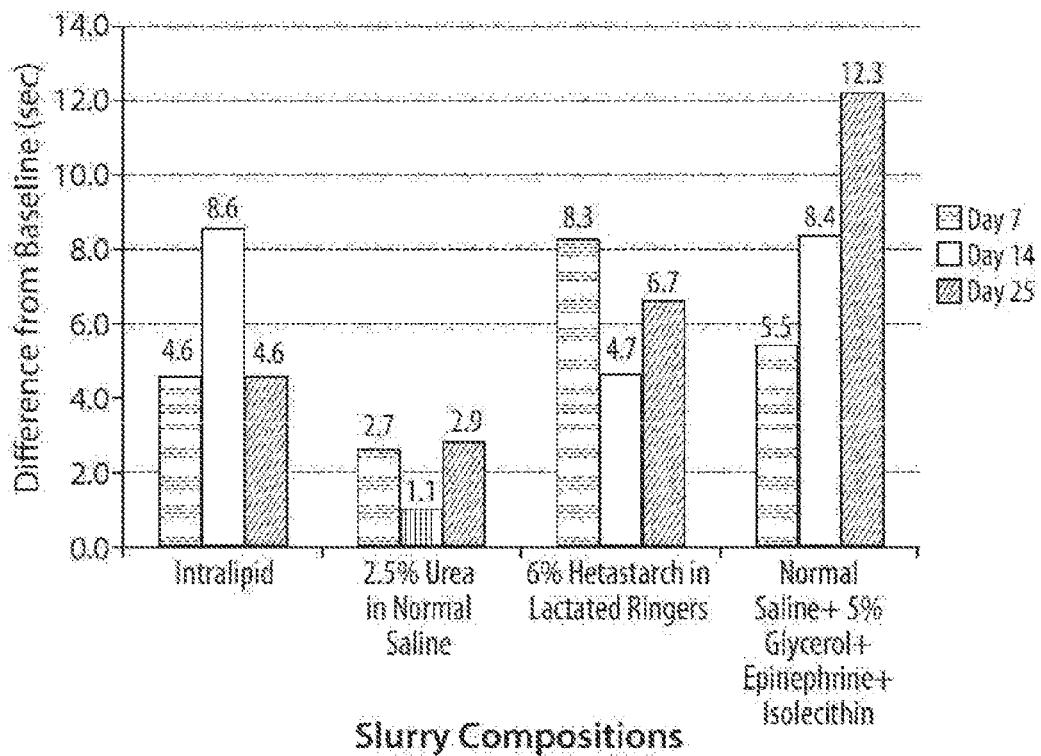
FIG. 18 depicts the difference in thermal withdrawal latencies of the left hindpaw at time of follow-up as compared to baseline measurements. A positive value indicates an increased tolerance for thermal pain due to decreased sensation.
Figure 19:
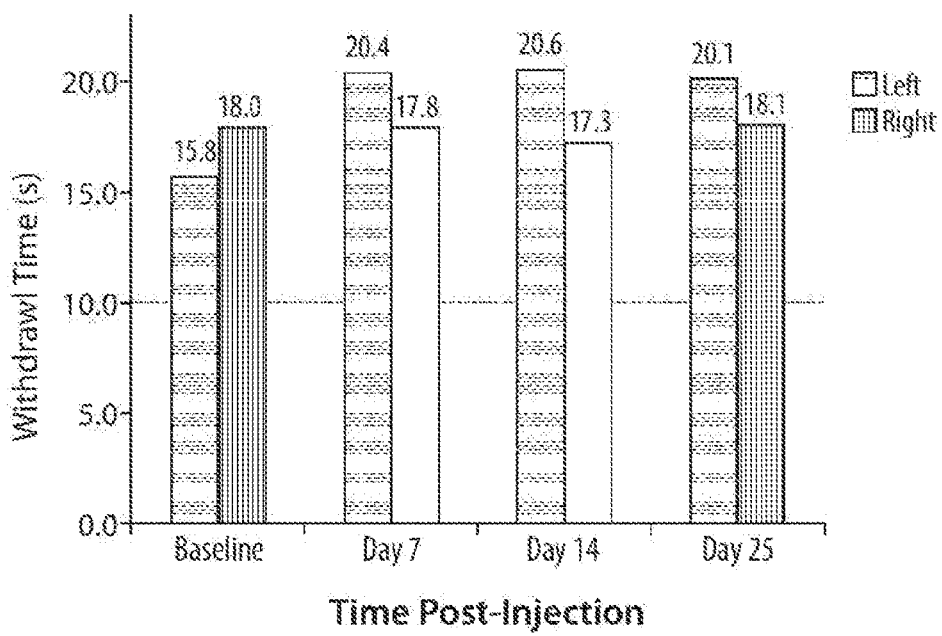
FIG. 19 depicts mean thermal withdrawal latency of rats injected with slurries. Slurries were injected through a needle around the left sciatic nerve and the right sciatic nerve was left untreated to serve as control.

*Intralipid: 20% Intravenous fat emulsion: 20% soybean oil, 1.2% egg yolk phospholipids (lecithin), 2.25% glycerin, water and sodium hydroxide to adjust pH
**Dosing of chemical agents: Epinephrine: 1:1,000 diluted, 0.05 cc in 10 cc of slurry, Isolecithin: 10 mg/ml 1 ml in 10 cc of slurry All of the rats tolerated the procedure well and no adverse effects at the site of injection were observed during follow-up. The rats underwent subsequent sensory testing on days 7, 14 and 25 post-slurry injection (FIG. 18). When compared to baseline, there was an increased thermal withdrawal latency of the hindpaw injected with slurry on follow-up days 7, 14 and 25 post-slung injection. This increase in thermal latency reflects an increased tolerance for thermal pain, which is indicative of anesthesia in the left hindpaw. The difference between left (slurry injected) and right (no injection) thermal withdrawal latencies is shown in FIG. 19. The thermal withdrawal latencies of the left hindpaw (which received the slurry injection) increase, whereas the right remain relatively stagnant (no change).

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

REFERENCES

All patents, patent applications and publications mentioned in this specification are herein incorporated by reference to the same extent as if each independent patent and publication was specifically and individually indicated to be incorporated by reference. Incorporation by reference herein includes, but is not limited to:

1. Lenz H, Goertz W, Preussler H. The freezing threshold of the peripheral motor nerve: an electrophysiological and light-microscopical study on the sciatic nerve of the rabbit. Cryobiology 1975; 12:486-96.
2. Barnard D. The effects of extreme cold on sensory nerves. Ann R Coll Surg Engl 1980; 62:180-7.
3. Kauffeld M, Wang M J, Goldstein V, Kasza K E. Ice Slurry Applications. Int J Refrig 2010; 33:1491-505.
4. Shikanov S, Wille M, Large M, et al. Microparticulate ice slurry for renal hypothermia: laparoscopic partial nephrectomy in a porcine model. Urology 2010; 76:1012-6.
5. Vanden Hoek T L, Kasza K E, Beiser D G, et al. Induced hypothermia by central venous infusion: saline ice slurry versus chilled saline. Crit Care Med 2004;32:S425-31.
6. Garbay B, Heape A M, Sargueil F, Cassagne C. Myelin synthesis in the peripheral nervous system. Prog Neurobiol 2000; 61:267-304.
7. Halkier-Sorensen, L. and K. Thestrup-Pedersen, The relevance of low skin temperature inhibiting histamine-induced itch to the location of contact urticarial symptoms in the fish processing industry. Contact dermatitis, 1989. 21(3): p. 179-83.
8. Fruhstorfer, H., M. Hermanns, and L. Latzke, The effects of thermal stimulation on clinical and experimental itch. Pain, 1986. 24(2): p. 259-69.
9. Pradel, W., et al., Cryosurgical treatment of genuine trigeminal neuralgia. Br J Oral Maxillofac Surg, 2002. 40(3): p. 244-7.
10. Calandria, L., Cryoanalgesia for post-herpetic neuralgia: a new treatment. Int J Dermatol. 2011. 50(6): p. 746-50.
11. Hargreaves K, Dubner R, Brown F, Flores C, Joris J (1988). A new and sensitive method for measuring thermal nociception in cutaneous hyperalgesia. Pain 32: 77-88.
12. Mitchell J. Degeneration of Non-myelinated Axons in the Rat Sciatic Nerve Following Lysolecithin Injection. Acta Neuropathol (Berl) (1982) 56:187-193.

The invention claimed is:

1. A method of providing reversible inhibition of one or more peripheral nerves by tissue cooling to a subject in need thereof, said method comprising:
    (1) accessing tissue comprising one or more peripheral nerves; and
    (2) injecting a biocompatible ice slurry into or around the one or more peripheral nerves, wherein:
    the biocompatible ice slurry cools the one or more peripheral nerves for a duration sufficient to inhibit the one or more peripheral nerves in the subject; and
    said inhibition is reversible.
2. The method of claim 1, wherein the biocompatible ice slurry comprises ice particles and one or more of a lactated Ringer's solution, an electrolyte solution, or a lactated electrolyte solution.
3. The method of claim 2, wherein the biocompatible ice slurry further comprises at least one of:
    hetastarch;
    dextrose;
    about 0.1% to about 20% glucose;
    about 0.1% to about 20% glycerol; or
    about 0.1% to about 6% hetastarch.
4. The method of claim 1, wherein the biocompatible ice slurry comprises ice particles and saline.
5. The method of claim 1, wherein the biocompatible ice slurry further comprises at least one of:
    about 0.1% to about 20% dextrose;
    about 0.1% to about 5% ethanol; or
    about 0.1% to about 10% poly vinyl alcohol.
6. The method of claim 1, wherein the biocompatible ice slurry further comprises at least one sugar, ion, polysaccharide, lipid, oil, lysolecithin, amino acid, caffeine, surfactant, antimetabolite, detergent, or a combination thereof.
7. The method of claim 6, wherein at least one of the following applies:
    the at least one sugar is glucose, mannitol, hetastarch, sucrose, sorbitol, or a combination thereof;
    the at least one ion is calcium, potassium, hydrogen, chloride, magnesium, sodium, lactate, phosphate, zinc, sulfur, nitrate, ammonium, carbonate, hydroxide, iron, barium, salts, or a combination thereof;

the at least one oil is canola oil, coconut oil, corn oil, cottonseed oil, flaxseed oil, olive oil, palm oil, peanut oil, safflower oil, soybean oil, sunflower oil, or a combination thereof;

the at least one surfactant is a detergent; or the at least one detergent is at least one of deoxycholate, sodium tetradecyl sulphate, polidocanol, sodium tetradecyl sulphate, polidocanol, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), a sorbitan ester, a poloxamer, or a combination thereof.

8. The method of claim 1, wherein the biocompatible ice slurry comprises a peritoneal dialysis solution.

9. The method of claim 1, wherein injecting the biocompatible ice slurry into or around the one or more peripheral nerves comprises providing the biocompatible ice slurry along a perineural sheath of the one or more peripheral nerves.

10. The method of claim 1, wherein the one or more peripheral nerves are somatic nerves.

11. The method of claim 10, wherein the somatic nerves are sensory nerves, motor nerves, cranial nerves, or spinal nerves.

12. The method of claim 1, wherein the biocompatible ice slurry cools the one or more peripheral nerves to between about 5° C. and about −40° C.

13. The method of claim 1, wherein the biocompatible ice slurry has a first equilibration temperature of between about 4° C. and about −30° C.

14. The method of claim 13, wherein the biocompatible ice slurry has a second equilibration temperature of between about 2° C. and about −30° C.

15. The method of claim 1, wherein the biocompatible ice slurry comprises ice particles that are spherical or round with a diameter of about 1 mm to about 0.01 mm.

16. The method of claim 1, wherein the biocompatible ice slurry further comprises an agent selected from the group consisting of a vasoconstricting agent, a corticosteroid, a nonsteroidal anti-inflammatory drug (NSAID), an anesthetic, a glucocorticoid, a lipoxygenase inhibitor, and combinations thereof.

17. The method of claim 16, wherein the vasoconstricting agent is epinephrine or norepinephrine.

18. The method of claim 16, wherein the anesthetic is selected from the group consisting of lidocaine, bupivacaine, prilocaine, tetracaine, procaine, mepivacaine, etidocaine, N-ethyllidocaine, QX-314, and combinations thereof.

19. The method of claim 1, wherein the one or more peripheral nerves are selected from the group consisting of a cutaneous nerve, a trigeminal nerve, an ilioinguinal nerve, an intercostal nerve, an interscalene nerve, a supraclavicular nerve, an infraclavicular nerve, an axillary nerve, a paravertebral nerve, a transverse abdominis nerve, a genitofemoral nerve, a lumbar plexus nerve, a femoral nerve, a pudendal nerve, a celiac plexus nerve, and a sciatic nerve.

20. The method of claim 1, wherein the biocompatible ice slurry is injected into or around the one or more peripheral nerves of the subject by tumescent pumping of the slurry.

21. The method of claim 1, further comprising administering pressure to reduce blood flow at the site of injection.

22. The method of claim 1, further comprising monitoring the biocompatible ice slurry by ultrasound or imaging.

23. The method of claim 1, wherein the inhibition is reversed after about 5 months or less.

24. The method of claim 1, wherein the subject suffers from hyperhidrosis disorder.

25. The method of claim 1, further comprising cooling a tissue surrounding the one or more peripheral nerves prior to injecting, during, or after injecting the biocompatible ice slurry.

* * * * *

UNITED STATES PATENT AND TRADEMARK OFFICE
CERTIFICATE OF CORRECTION

| | |
|---|---|
| PATENT NO. | : 11,826,427 B2 |
| APPLICATION NO. | : 17/236567 |
| DATED | : November 28, 2023 |
| INVENTOR(S) | : Garibyan et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this
Third Day of December, 2024

Katherine Kelly Vidal
*Director of the United States Patent and Trademark Office*